United States Patent
Collins et al.

(10) Patent No.: US 9,210,970 B2
(45) Date of Patent: Dec. 15, 2015

(54) TOUCH FASTENING

(71) Applicant: Velcro Industries B.V., Willemstad, Curacao (NL)

(72) Inventors: Andrew Collins, Bedford, NH (US); Christopher M. Gallant, Nottingham, NH (US)

(73) Assignee: Velcro Industries B.V., Willemstad, Curacao ( * ) Notice: Subject to any disclaimer, the term of this patent is extended or adjusted under 35 U.S.C. 154(b) by 67 days.

(21) Appl. No.: 14/053,701

(22) Filed: Oct. 15, 2013

(65) Prior Publication Data

US 2014/0103567 A1 Apr. 17, 2014

Related U.S. Application Data

(60) Provisional application No. 61/713,962, filed on Oct. 15, 2012.

(51) Int. Cl.
*A44B 18/00* (2006.01)
*B29C 43/22* (2006.01)
*B29C 43/46* (2006.01)
*B29C 47/32* (2006.01)
*B29C 43/00* (2006.01)
(Continued)

(52) U.S. Cl.
CPC ........ *A44B 18/0015* (2013.01); *A44B 18/0019* (2013.01); *A44B 18/0049* (2013.01); *A44B 18/0065* (2013.01); *B29C 43/222* (2013.01); *B29C 43/46* (2013.01); *A61F 13/581* (2013.01); *A61F 13/62* (2013.01); *A61F 13/625* (2013.01); *B29C 43/003* (2013.01); *B29C 47/32* (2013.01); *B29C 2043/461* (2013.01); *B29C 2045/465* (2013.01); *Y10T 24/2783* (2015.01)

(58) Field of Classification Search
None
See application file for complete search history.

(56) References Cited

U.S. PATENT DOCUMENTS 3,900,652 A 8/1975 Uraya et al.
4,894,060 A 1/1990 Nestegard
(Continued)

FOREIGN PATENT DOCUMENTS

DE 19828856 10/1999
DE 19906008 8/2000
(Continued)

OTHER PUBLICATIONS

International Search Report and Written Opinion Int'l Application No. PCT/EP2013/071450 mailed May 16, 2014.

*Primary Examiner* — Jeffrey Wollschlager
(74) *Attorney, Agent, or Firm* — Fish & Richardson P.C.

(57) ABSTRACT

A method of forming a touch fastener product having a sheet-form base and an array of discrete fastener elements each extending from the base includes providing a molded sheet-form base and an array of discrete fastener element preforms, each preform extending from the base and including both a stem portion rising from the base and a head portion both contiguous with a distal end of the stem portion and having an upper surface directed away from the base, the head portion including at least one laterally directed extension overhanging the base in a primary lateral direction between exposed sides of the fastener element preform and ending at a distal, free tip; and then forming respective caps, of a cap material of a higher flex modulus than the resin of the preforms, on the upper surfaces of at least some of the molded fastener element preforms to form the discrete fastener elements.

18 Claims, 18 Drawing Sheets

(51) Int. Cl.
*A61F 13/58* (2006.01)
*A61F 13/62* (2006.01)
*B29C 45/46* (2006.01)

(56) References Cited

U.S. PATENT DOCUMENTS

| | | | |
|---|---|---|---|
| 5,035,029 A | | 7/1991 | Horita et al. |
| 5,221,276 A | * | 6/1993 | Battrell ................ 604/389 |
| 5,604,963 A | * | 2/1997 | Akeno ................... 24/452 |
| 5,636,414 A | * | 6/1997 | Litchholt ............... 24/304 |
| 5,692,271 A | | 12/1997 | Provost et al. |
| 5,736,216 A | | 4/1998 | Shibahara et al. |
| 5,786,061 A | * | 7/1998 | Banfield ................ 428/100 |
| 6,162,040 A | | 12/2000 | Clune |
| 6,163,939 A | | 12/2000 | Lacey et al. |
| 6,180,205 B1 | | 1/2001 | Tachauer et al. |
| 6,287,665 B1 | * | 9/2001 | Hammer ................ 428/100 |
| 6,393,673 B1 | * | 5/2002 | Kourtidis et al. ........ 24/304 |
| 6,428,525 B1 | * | 8/2002 | Malowaniec .......... 604/389 |
| 6,569,374 B1 | * | 5/2003 | Poulakis ................ 264/447 |
| 6,572,727 B1 | * | 6/2003 | Schulte ................. 156/278 |
| 6,627,133 B1 | * | 9/2003 | Tuma .................... 264/167 |
| 6,699,560 B1 | * | 3/2004 | Schulte ................... 428/95 |
| 6,701,580 B1 | * | 3/2004 | Bandyopadhyay ...... 24/16 R |
| 6,904,649 B2 | * | 6/2005 | VanBenschoten et al. ..... 24/452 |
| 7,008,589 B1 | * | 3/2006 | Poulakis ................ 264/470 |
| 7,048,818 B2 | | 5/2006 | Krantz et al. |
| 7,052,638 B2 | | 5/2006 | Clarner et al. |
| 7,056,462 B2 | | 6/2006 | Provost et al. |
| 7,198,743 B2 | * | 4/2007 | Tuma .................... 264/167 |
| 7,373,700 B2 | | 5/2008 | Martin et al. |
| 7,445,741 B2 | | 11/2008 | Poulakis et al. |
| 7,807,007 B2 | | 10/2010 | Tachauer et al. |
| 8,079,995 B2 | | 12/2011 | Tachauer et al. |
| 8,082,637 B2 | * | 12/2011 | Tolan et al. ............. 24/452 |
| 8,168,103 B2 | * | 5/2012 | Cheng ................... 264/167 |
| 8,388,880 B2 | * | 3/2013 | Tuma .................... 264/250 |
| 2002/0116799 A1 | * | 8/2002 | Martin et al. ........... 24/452 |
| 2002/0138064 A1 | * | 9/2002 | Datta et al. ............. 604/391 |
| 2002/0162197 A1 | * | 11/2002 | Romanko et al. ....... 24/306 |
| 2003/0085492 A1 | * | 5/2003 | Schulte ................. 264/443 |
| 2004/0088835 A1 | | 5/2004 | Tachauer et al. |
| 2005/0081344 A1 | * | 4/2005 | Clarner .................. 24/452 |
| 2005/0081346 A1 | * | 4/2005 | Clarner .................. 24/452 |
| 2005/0246873 A1 | * | 11/2005 | Tachauer et al. ........ 24/451 |
| 2006/0216461 A1 | * | 9/2006 | Tachauer et al. ........ 428/99 |
| 2007/0036939 A1 | * | 2/2007 | Ferry (Hinton) et al. ..... 428/100 |
| 2008/0050553 A1 | * | 2/2008 | Tuma .................... 428/99 |
| 2008/0143007 A1 | * | 6/2008 | Tuma .................... 264/78 |
| 2009/0311438 A1 | * | 12/2009 | Poulakis ................ 427/540 |
| 2010/0130925 A1 | | 5/2010 | Haslinger et al. ........ 604/96.01 |
| 2010/0145147 A1 | | 6/2010 | Pinsky et al. ........... 600/114 |
| 2011/0265293 A1 | | 11/2011 | Idrizovic et al. |
| 2013/0256954 A1 | | 10/2013 | Libby et al. |

FOREIGN PATENT DOCUMENTS

| | | |
|---|---|---|
| EP | 894448 | 5/2001 |
| EP | 754415 | 12/2001 |
| WO | WO 9857565 | 12/1998 |
| WO | WO 0132044 | 5/2001 |

* cited by examiner

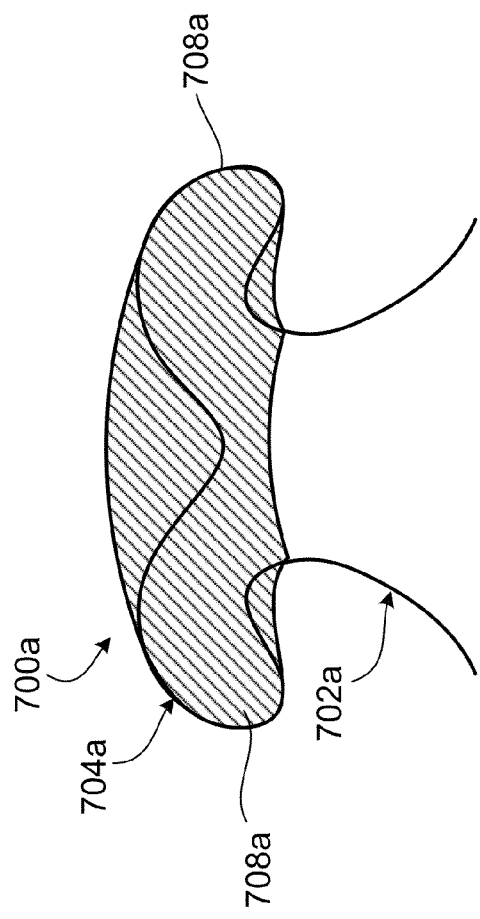
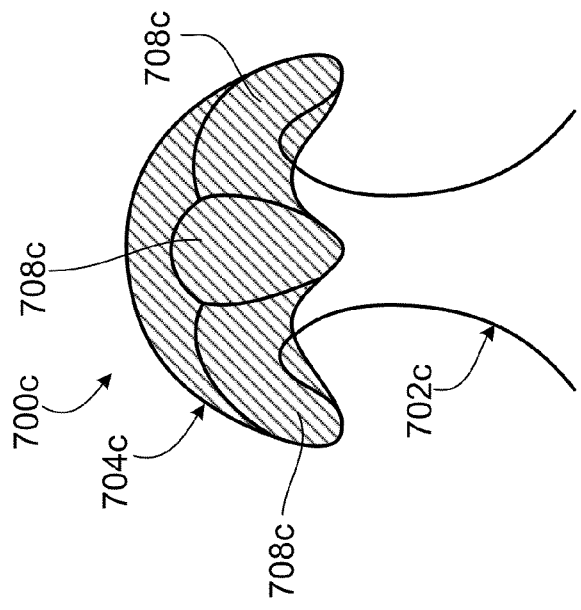
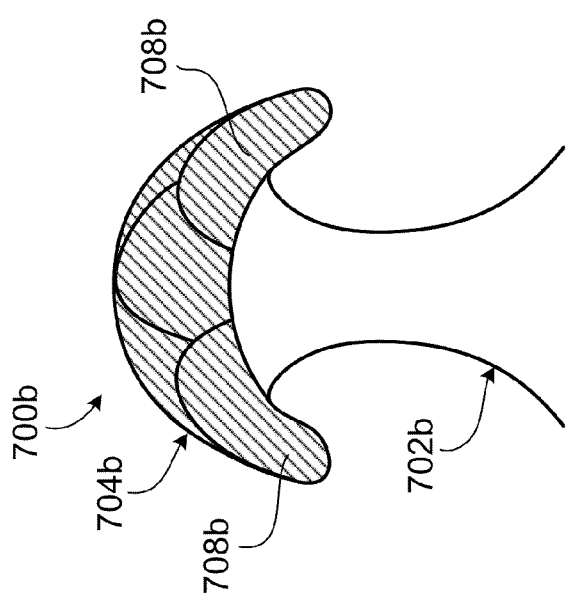

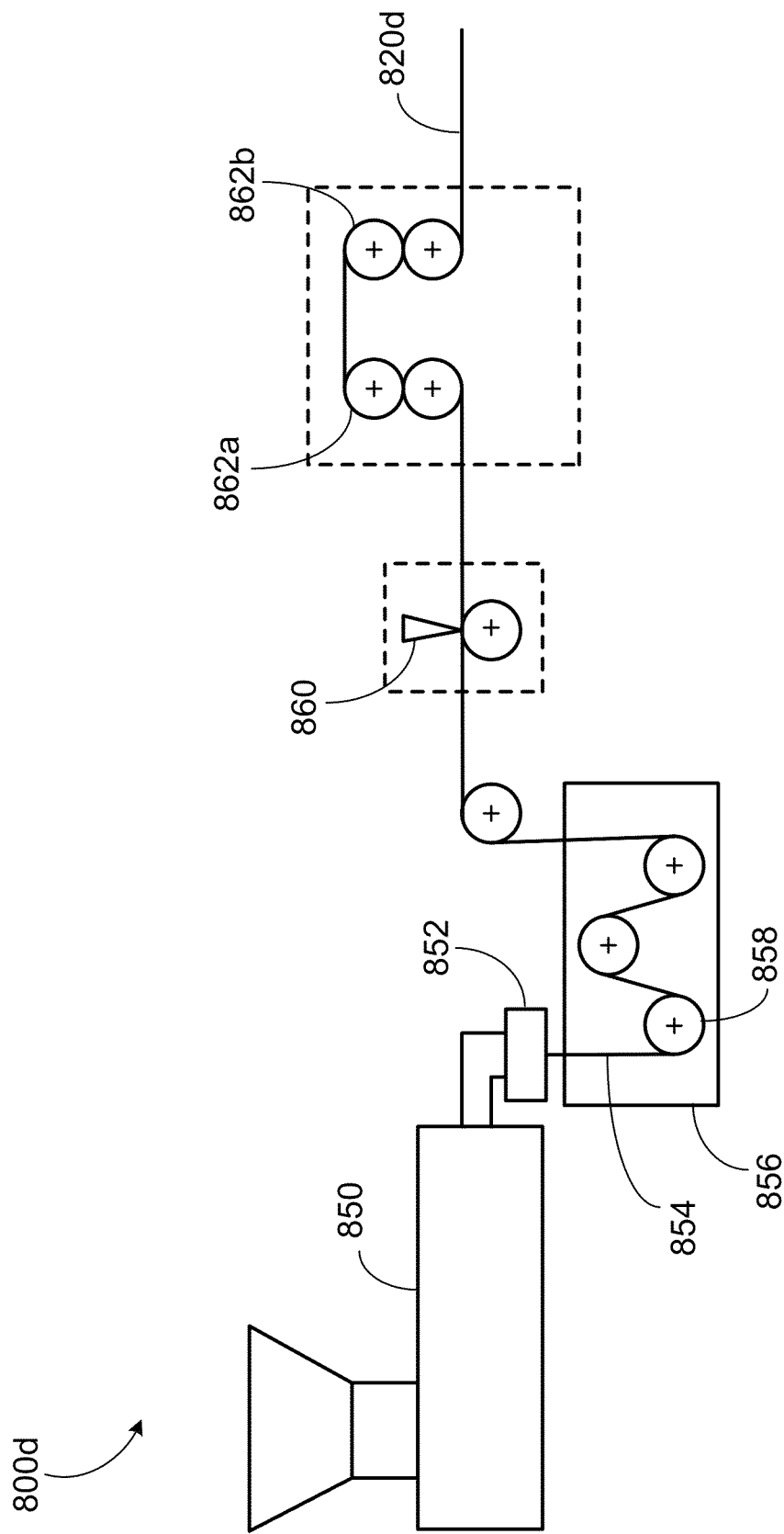

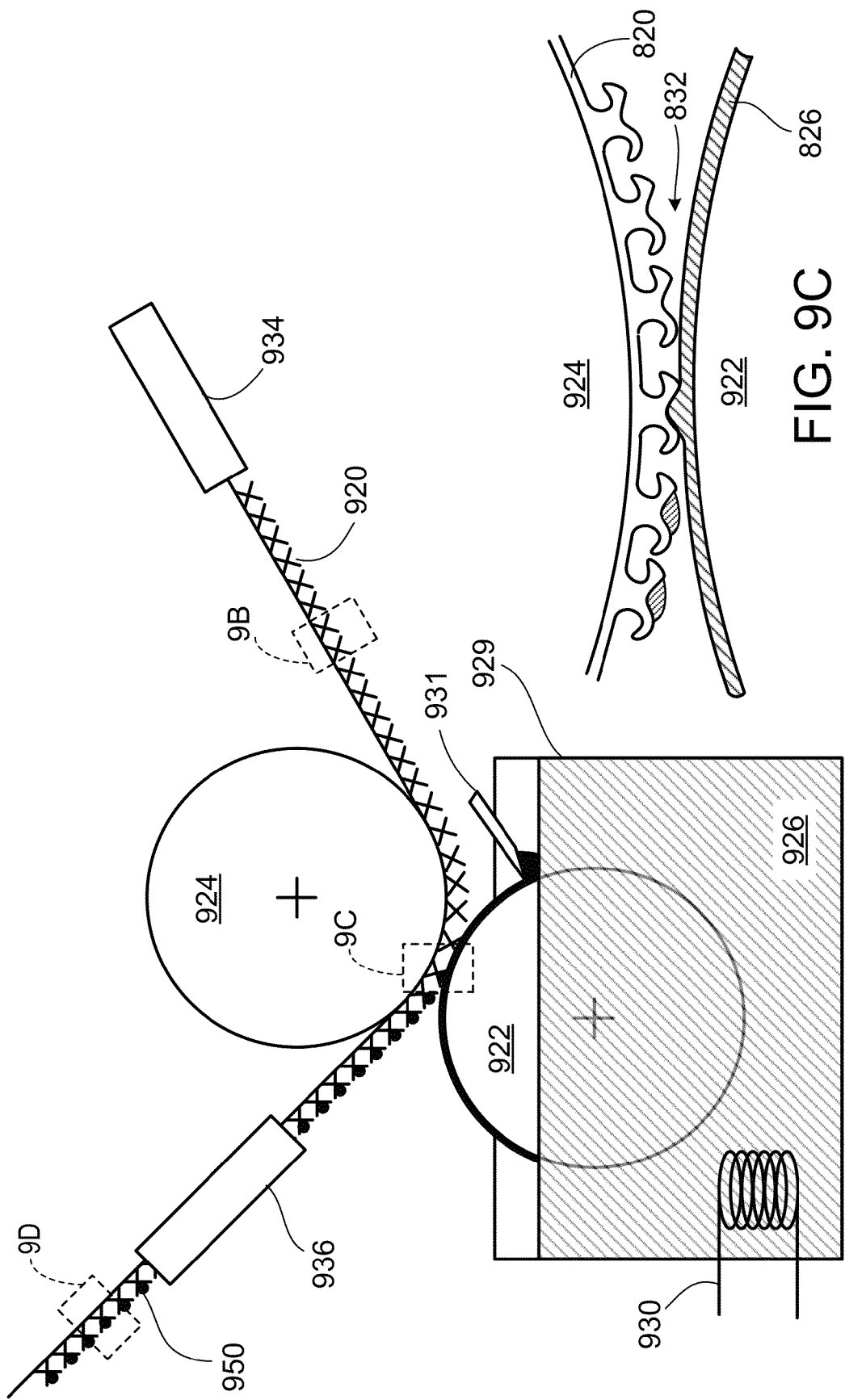

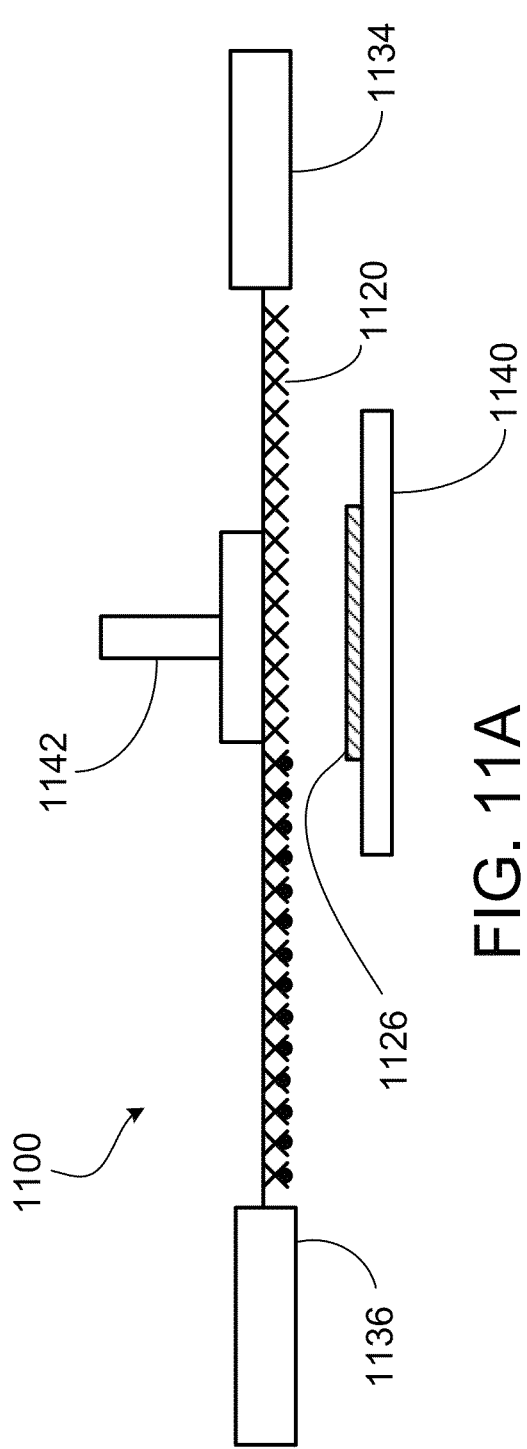
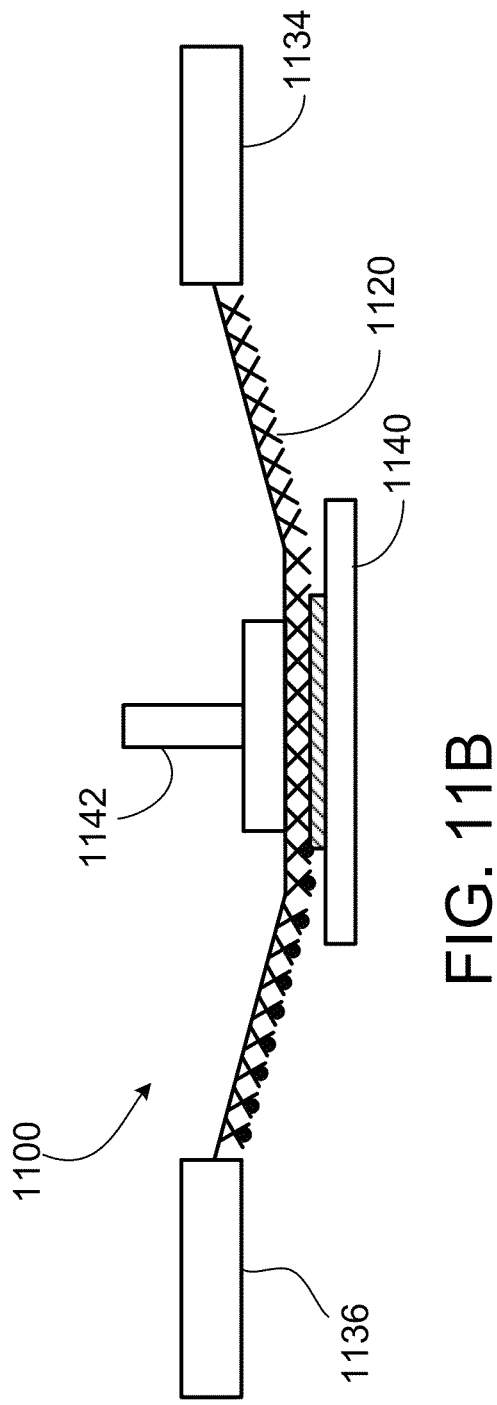

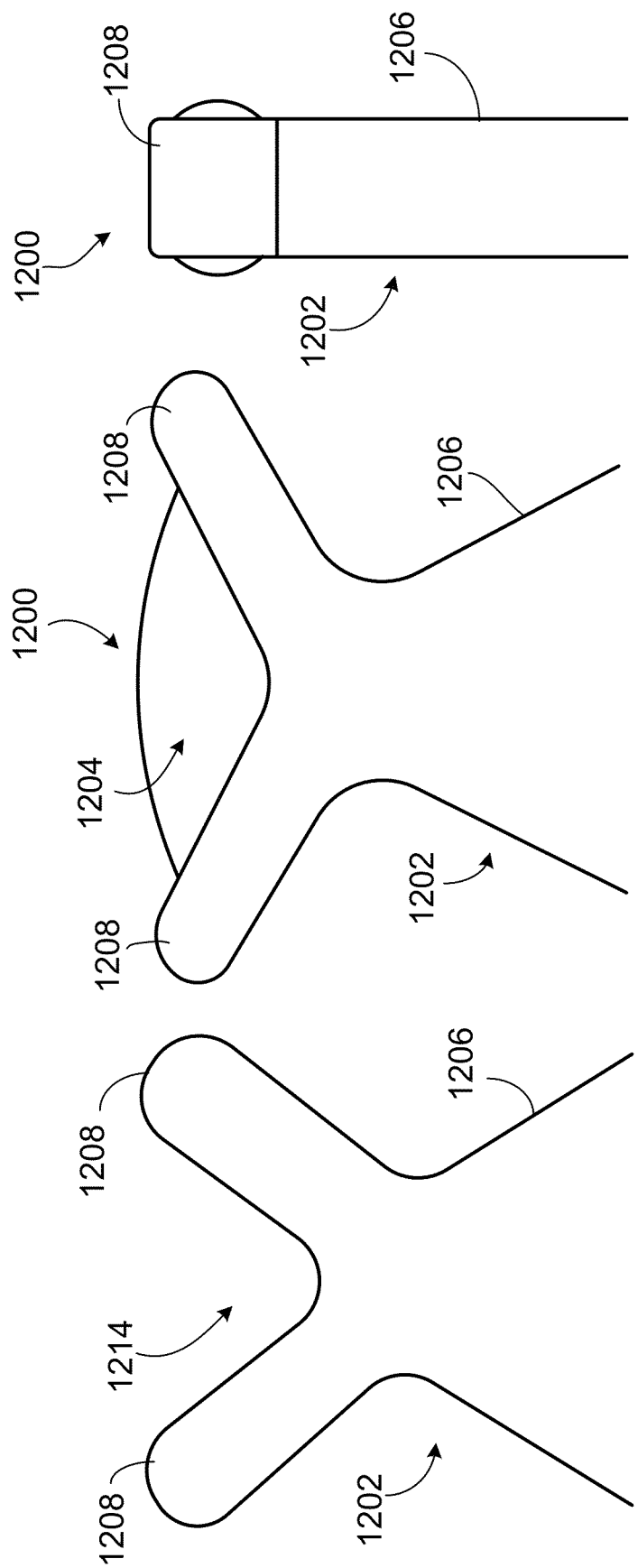

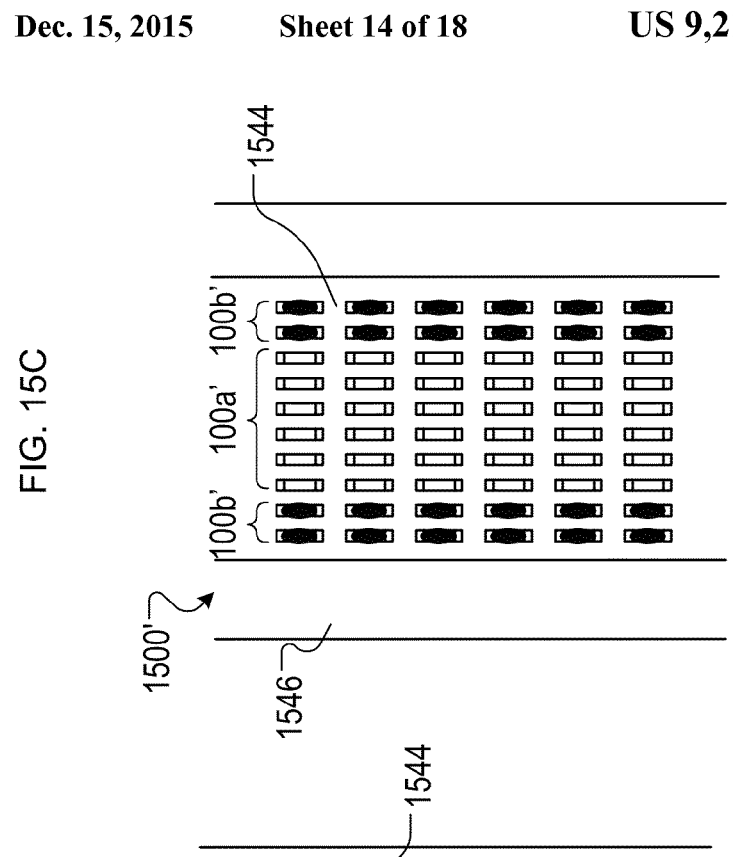
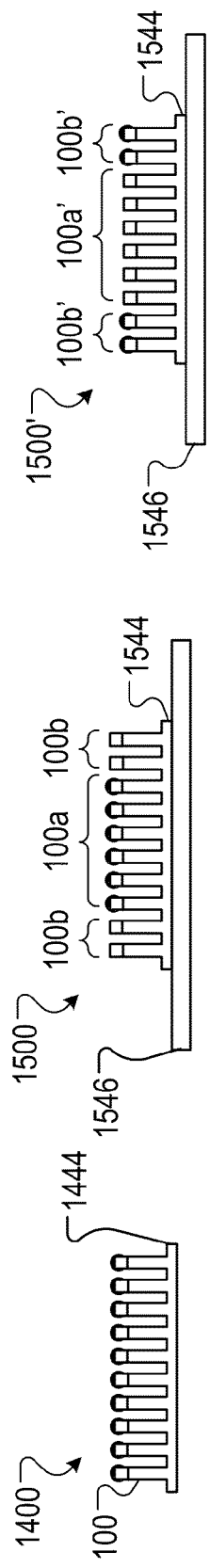
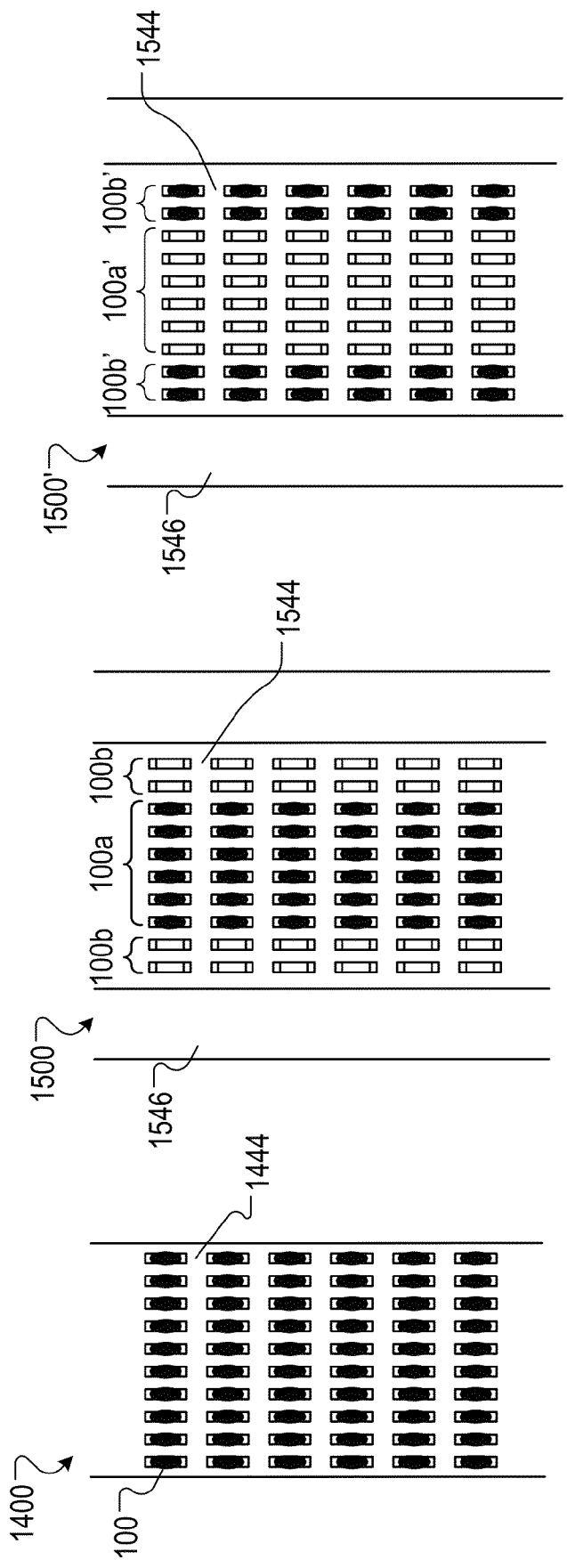
FIG. 15C
FIG. 15D
FIG. 15A
FIG. 15B
FIG. 14A
FIG. 14B

TOUCH FASTENING

TECHNICAL FIELD

This specification generally relates to touch fasteners, such as those featuring arrays of discrete, miniature structures for releasably engaging with a mating material, such as a loop or cooperative structural array.

BACKGROUND

A number of touch fastening systems, such as those found in personal care and other products, feature arrays of discrete hooking structures that extend from a common base. Many such products are formed from resin, such as by molding the base and hooking structures from a unitary resin flow, or severing the rails of a plastic extrusion, or by molding the base with preform structures (e.g., straight stems) that are later deformed to create hooking structures. Some hooking structures are hook-shaped, with tips that extend in a primary lateral direction to define a crook. Some hooking structures have multiple crooks, with an example being a 'palm tree' structure with tips extending in two opposite directions. Some hooking structures are known as 'mushroom-type' and feature engaging heads that overhang the base all around a supporting stem.

Molding overhanging heads in non-opening cavities requires selecting a resin and a hooking element shape that will allow the molded elements to temporarily deform while being withdrawn from the mold, and that will also provide a desired level of peel resistance during use.

Improvements are continuously sought to facilitate the manufacture of fastener products with desired properties, including peel and shear strength and touch softness.

SUMMARY

One or more aspects of the invention draws from the realization that by applying a structural material to upper portions of already formed elements, under certain circumstances, improvements in the fastening performance of a resulting touch fastener product can be obtained while also allowing for other desirable properties, such as a desired feel to the touch.

In one aspect, the invention features a method of forming a touch fastener product having a sheet-form base and an array of discrete fastener elements each extending from the base. The method includes providing a sheet-form base and an array of discrete fastener element preforms of resin, each preform extending from the base and including both a stem portion rising from the base and a head portion both contiguous with a distal end of the stem portion and having an upper surface directed away from the base, the head portion including at least one laterally directed extension overhanging the base in a primary lateral direction between exposed sides of the fastener element preform and ending at a distal, free tip; and then forming respective caps, of a cap material of a higher flex modulus than the resin of the preforms, on the upper surfaces of at least some of the fastener element preforms to form the discrete fastener elements.

In some examples, the head portion of each fastener element preform has two oppositely directed extensions separately overhanging the base and ending in respective distal tips.

In some applications, the caps are formed such that the tips of the head portions of the discrete fastener element preforms remain free of the cap material.

In some cases, the caps are formed such that regions of the upper surfaces of the head portions of the fastener element preforms adjacent the tips remain free of the cap material.

In some embodiments, the caps are formed such that undersides of the head portion extensions remain free of the cap material.

In some implementations, the caps are formed such that the stem portions of the fastener element preforms remain free of the cap material.

In some applications, the caps are formed to extend laterally beyond the exposed sides of the fastener element preforms.

In some cases, the caps are formed to extend laterally beyond the upper surfaces of the fastener element preforms, to overhang the base. In some examples, the caps are formed to overhang the base only in limited lateral directions.

In some embodiments, the upper surface of each head portion defines a central recess bounded on two opposite sides by the upper surface and laterally open on the sides of the fastener element preform, and wherein the caps are formed to fill the central recesses. In some applications, the caps are formed to have convex upper surfaces disposed over the recesses.

In some examples, the caps, as formed, extend farther from the base than the upper surfaces of the fastener element preforms.

In some cases, at least one of the exposed sides of each fastener element preform is planar.

In some applications, the cap material is a thermoplastic resin.

In some implementations, forming the caps includes contacting the upper surfaces of the fastener element preforms with a quantity of liquid cap material carried on a cap material source, and then withdrawing the fastener element preforms from the cap material source, whereby a portion of the quantity of cap material is drawn off of the cap material source and remains on the fastener element preform. In some embodiments, forming the caps further includes allowing the cap material to form a free-form exposed cap surface on the fastener element preforms before solidifying. In some applications, the cap material source includes an outer surface of a rotating drum, and wherein forming the caps includes passing the molded fastener element preforms adjacent the drum outer surface, such that cap material carried on the outer surfaces contacts the upper surfaces of the fastener element preforms. In some examples, the drum is configured such that only some of the fastener element preforms contact liquid cap material carried on the drum outer surface.

In some cases, providing the molded sheet-form base and array of discrete fastener element preforms includes continuously molding the form base and array of discrete fastener element preforms from a contiguous flow of resin.

In another aspect, the invention features a method of forming a touch fastener product having a sheet-form base and an array of discrete fastener elements each extending from the base. The method includes: providing a molded sheet-form base and an array of discrete fastener element preforms, each preform extending from the base and having an upper surface directed away from the base; and then adding resin to the upper surfaces of the preforms to form respective caps of the added resin on the upper surfaces to form the discrete fastener elements, the caps formed to extend laterally beyond the upper surfaces, to overhang the base.

In some examples, the fastener element preforms include both a stem portion rising from the base and a head portion both contiguous with a distal end of the stem portion, the head portion laterally overhanging the base. In some applications, the head portion of each fastener element preform has two oppositely directed extensions separately overhanging the base and ending in respective distal tips. In some implementations, the caps are formed such that the tips of the head portions of the discrete fastener element preforms remain free of the added resin. In some embodiments, the upper surface of each head portion defines a central recess bounded on two opposite sides by the upper surface and laterally open on at least one side of the fastener element preform, and wherein the caps are formed to fill the central recesses.

In some implementations, the caps are formed only on fastener element preforms near an edge of the array of discrete fastener element preforms, leaving fastener element preforms farther from the edge free of the added resin, and wherein the added resin is softer than a material used to mold the fastener element preforms.

In some applications, the base is molded on a supporting substrate extending laterally beyond the base. In some embodiments, the substrate includes a fibrous sheet, the base molded such that the resin encapsulates surface fibers of the fibrous sheet. In some implementations, the substrate includes a film or a paper sheet. In some examples, the base has an edge adjacent exposed surface of the supporting substrate. In some embodiments, the base forms a bounded lane having two opposite edges extending along the supporting substrate. In some applications, the caps are formed such that fastener element preforms adjacent the base edge remains free of the added resin. In some applications, the base is bounded on all lateral sides by exposed surface of the supporting substrate.

In some examples, providing the molded sheet-form base and array of discrete fastener element preforms includes continuously molding the form base and array of discrete fastener element preforms from a contiguous flow of resin.

In yet another aspect, the invention features a method of forming a touch fastener product having a sheet-form base and an array of fastener elements each extending from the base. The method includes: providing an array of discrete fastener element preforms, each preform including a stem portion rising from the sheet-form base and a directed head portion contiguous with a distal end of the stem portion, the head portion overhanging the base in at least one lateral direction; and then forming respective caps on the head portions of at least some of the molded fastener element preforms to form the discrete fastener elements, the caps extending beyond the head portions to overhang the base in at least one lateral direction.

In yet another aspect, the invention features a method of forming a touch fastener product having a sheet-form base and an array of fastener elements each extending from the base. The method includes: providing a molded array of discrete upstanding stems, each stem rising from the sheet-form base to terminate in a distal end having an upper surface directed away from the base; deforming the distal ends of the stems to form fastener element preforms, each preform including a stem portion and a head portion contiguous the stem portion, the head portion overhanging the base in at least one lateral direction; and then forming respective caps, of a cap material having a different composition than the moldable resin, on the head portions of at least some of the fastener element preforms to form the discrete fastener elements.

In yet another aspect, the invention features a touch fastener product including: a sheet-form base; and an array of fastener elements each extending from the base, at least one of the fastener elements including: a fastener element preform including an upstanding molded stem; and a cap crowning an upper surface of the fastener element preform, the cap overhanging the base in at least one lateral direction and being composed of a material that is stiffer than a material of which the fastener element preform is composed.

In yet another aspect, the invention features a touch fastener product including: a sheet-form base; and an array of fastener elements each extending from the base, at least one of the fastener elements including: a fastener element preform including both a stem portion rising from the base and a head portion both contiguous with a distal end of the stem portion and having an upper surface directed away from the base, the head portion including at least one laterally directed extension overhanging the base in a primary lateral direction between exposed sides of the fastener element preform and ending at a distal, free tip; and a cap crowning an upper surface of the fastener element preform, the cap being composed of a material that is stiffer than a material of which the fastener element preform is composed.

The details of one or more implementations of the subject matter described in this specification are set forth in the accompanying drawings and the description below. Other features, aspects, and advantages of the subject matter will become apparent from the description, the drawings, and the claims.

BRIEF DESCRIPTION OF THE DRAWINGS

FIGS. 7A-7C are side views of various male fastener elements where the caps entirely envelop the heads of the preform structures.

FIG. 8D is a schematic view of a system for forming preform structures using a cut-and-stretch technique.

FIG. 9A is a schematic illustration of an apparatus and method for capping preform structures by reverse roll coating.

FIG. 9C is an enlarged view of the area marked FIG. 9C in FIG. 9A.

FIGS. 11A and 11B are sequential schematic views of a third apparatus for capping preform structures.

FIG. 12A is a side view of a preform structure having opposing heads extending both upward and laterally outward from a broad stem.

FIG. 12B is a cross-sectional side view of a capped fastener element including a deformed preform structure.

FIG. 12C is an end view of the capped fastener element of FIG. 12B.

FIGS. 14A and 14B are front and top views, respectively, of a fastener product featuring an array of capped fastener elements.

FIGS. 15A and 15B are front and top views, respectively, of a first example fastener product featuring an array of fastener elements including both capped and uncapped fastener elements.

FIGS. 15C and 15D are front and top views, respectively, of a second example fastener product featuring an array of fastener elements including both capped and uncapped fastener elements.

Like reference numbers and designations in the various drawings indicate like elements.

DETAILED DESCRIPTION

Figure 1A:
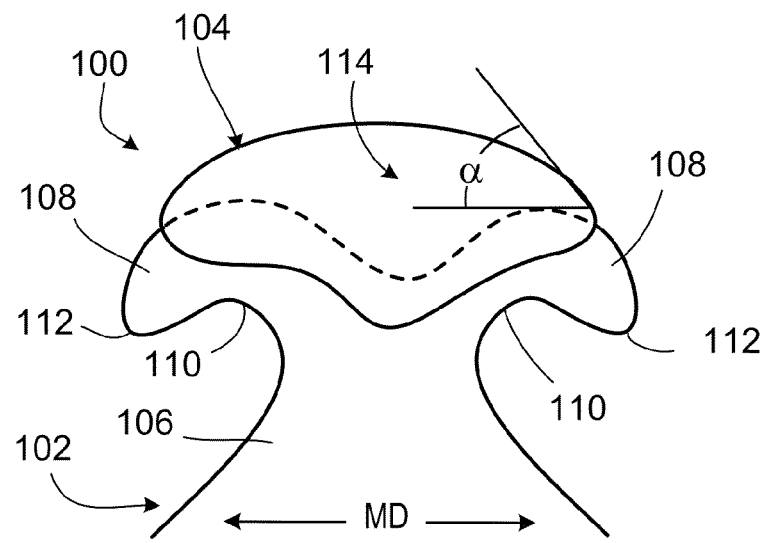
FIGS. 1A and 1B are side and end views, respectively, of a capped palm tree fastener element.
Figure 1B:
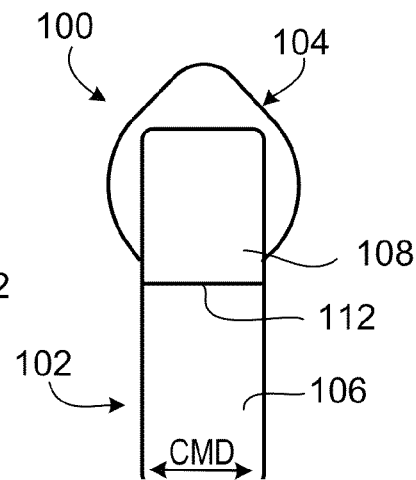

FIGS. 1A and 1B show a first example of a male fastener element 100. An array of such fastener elements can be carried on a sheet-form base (not shown) to provide a touch fastener product (see FIGS. 12A-15B). Fastener element 100 features a preform structure 102 and a cap 104 crowning the top of the structure. The preform structure and the cap can be formed from substantially identical or dissimilar materials to create a fastener element with desired structural and/or material characteristics. As one example, the preform structure and the cap can be formed from the same material to provide a uniform fastener element having a unique shape that would not be feasible using conventional manufacturing techniques. On the other hand, a non-uniform fastener element can be provided when the preform structure is formed from a particularly flexible resin material, while the cap material is particularly stiff (e.g., at least stiffer than the preform structure material). In this case, the flexibility of preform structure 102 can render the fastener element 100 "skin friendly", while the rigidity of cap 104 reinforces the preform structure to bolster the performance of the fastener element. This combination of features can be particularly useful when applied to fastening systems for personal care items, such as diaper training pants, panty liners, and incontinency garments, where a reliable fastening is required, but direct contact with a rigid fastener product can cause skin irritation.

In this example, preform structure 102 has a palm tree-shaped profile with relatively flat side surfaces, such as may be molded in a cavity formed between two adjacent mold plates in a mold roll as taught by Fischer in U.S. Pat. No. 4,775,310. Preform structure 102 includes a broad stem (or pedestal) 106 formed integrally with and rising from the supporting sheet-form base, and two opposing heads 108 contiguous with a distal end of the stem. Stem 106 is continuously tapered, defining an included angle between its front and rear edges. Heads 108 extend outward from stem 106 to overhang the base in opposite lateral directions. As shown, heads 108 define respective concave crooks 110 for engaging features of a mating fastener product (e.g., loop fibers). Each of heads 108 terminates in a distal re-entrant tip 112.

Cap 104 sits atop preform structure 102, on the upper surface of heads 108, and is bonded to the preform structure so as to be fixedly situated thereon. In this example, cap 104 is a bulbous, free-form structure (e.g., a non-molded structure) having relatively smooth, convex outer surfaces. The smooth outer surface of the cap may enhance the skin friendly feel of the fastener element to a user. As described in detail below, cap 104 can be formed on preform structure 102 by depositing an amount of liquid cap material on the structure, and allowing the liquid cap material to freely form under atmospheric pressure. In this case, the shape of the cap can be deliberately defined by, for example, controlling the "wettability" of the preform structure by the liquid cap material, as well as the viscosity of the cap material as applied. The amount of wetting directly corresponds to the contact angle $\alpha$ between the surface of the preform structure and the cap material. Generally, high wettability corresponds to a low contact angle, and low wettability corresponds to a high contact angle. In some implementations, it is advantageous to have relatively high wettability of the preform structures by the liquid cap material so that the contact angle is low, providing a smooth transition between the two constituents of the fastener element. This effect can also contribute to the skin friendly feel of the fastener element.

Wettability can depend on several factors, including the inherent surface tension of the liquid cap material and the natural imbalance of cohesion forces (i.e., the intermolecular attractive forces of the liquid cap material) and adhesion forces (the forces of attraction between the liquid cap material and the solidified material of the preform structures). These variables can be tuned by using material additives (either in the liquid cap material or the material used to mold the preform structures) and/or by conditioning or modifying the materials during manufacturing (e.g., implementing surface treatments on the preform structures to modify the surface energy, or by controlling the temperatures of the liquid cap material to modify the viscosity and surface tension).

Cap 104 fills a recess 114 defined between the divergent heads 108 of preform structure 102, thereby bridging the gap between the heads. The cap is positioned near the neck regions of the heads so as to brace or reinforce them against distension under peel loads. As shown, recess 114 is a trough, or a channel, that is bounded in the machine direction (i.e., the lateral direction of maximum overhang of the fastener element), labeled "MD", by the apex of each head 108. The recess is entirely unbounded or open in the cross-machine direction (i.e., the lateral direction perpendicular to the machine direction), labeled "CMD". The cap can extend laterally outward from, or spillover, the recess formed by the upper surface of the preform structure. In this example, cap 104 extends beyond the open sides of recess 114 to overhang the base in the cross-machine direction, offering an additional engagement feature (e.g., a loop engageable feature) to supplement crooks 110 (as seen in FIG. 1B) and also covers the upper edges of the hook, thereby improving the perceived softness of the product. As shown, cap 104 also extends above the apex of heads 108, increasing the overall height of fastener element 100. In the machine direction, the cap extends outward to a point near the apex of each head of the preform structure, such that at least a portion of the heads, the crooks, and the re-entrant tips are free of any cap material. Leaving the tips free of the cap material can, in some circumstances, avoid inhibiting the ability of the tips to snag loop fibers. The stem of the preform structure is also generally free of cap material, allowing the fastener element to readily flex in response to bending loads.

Preform structure 102 can be fashioned from a moldable resin material that includes a highly flexible polymer (or polymers), enabling the preform structure to readily bend and flex elastically in response to minimal amounts of pressure. When made of a highly flexible polymer, the heads of the preform structure are less likely to feel rough to a user. Polymers for molding particularly flexible preform structures can have a flexural modulus in a range of 7 kpsi (48 MPa) to 30 kpsi (207 MPa). Suitable flexible polymers can include, for example, common thermoplastic polymers such as polyamide and polypropylene, which can optionally be modified with block copolymers such as polyurethanes, copolyether esters, etc. U.S. Pat. No. 7,373,700, the entirety of which is incorporated by reference into the present disclosure, describes several types of appropriate polymers.

Cap 104 is fashioned from a different material than the preform structure material. The solidified cap material can be significantly stiffer than the material of the preform structure, as may be exhibited by a flexural modulus that is greater than that of the preform structure material. In one example, the rigid cap material has a flexural modulus of about 66 kpsi (456 MPa). For some applications, the flexural modulus of the cap material is at least about two times that of the preform structure material. Suitable rigid polymers can include, for example, acrylate or methacrylate resins (commonly referred to as acrylate or methacrylate plastics), and linear low-density polyethylene. In some examples, the cap material is curable in ultraviolet light or electron beam radiation.

Figure 1C:
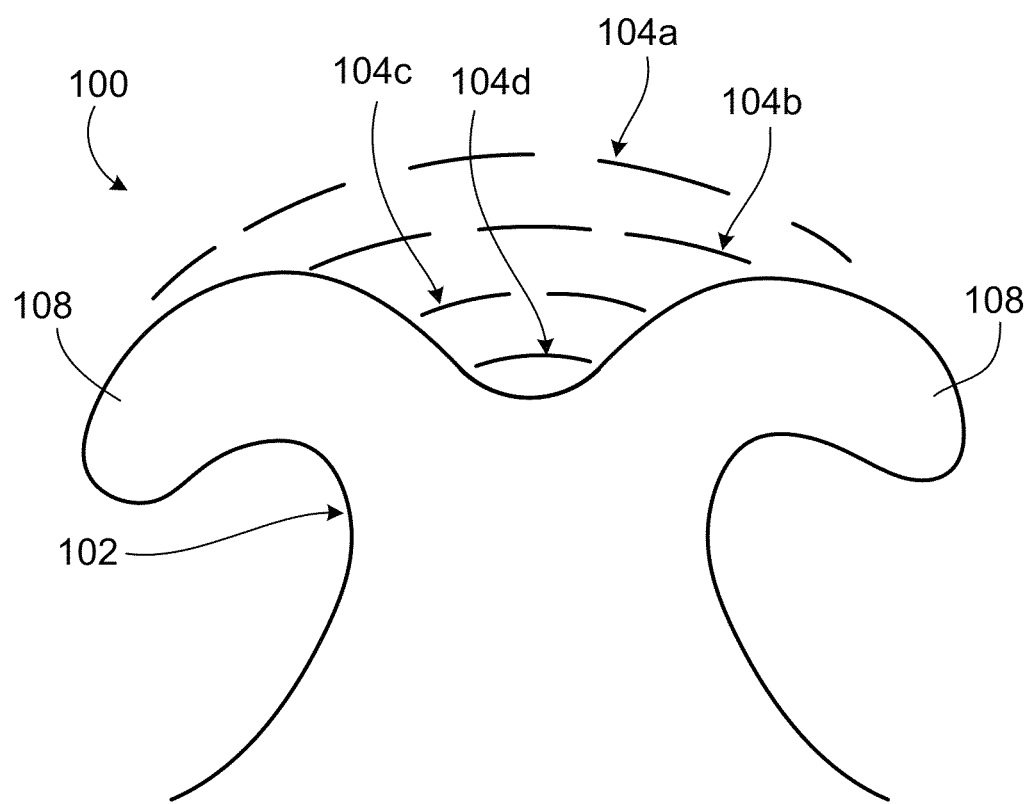
FIG. 1C is a diagram illustrating the preform structure of FIG. 1A with different cap sizes.

Customization of the fastener element characteristics can be achieved through selection of the materials used to fashion the preform structure and the cap. This type of customization may prove especially advantageous when it is not feasible or expedient to mold the preform structures in a desired final shape, or when the tooling for such molding would be too expensive or the processing time too long. The size of the cap provides another tuning parameter for customizing the fastener element characteristics, which can be altered with relative ease. FIG. 1C provides a diagram showing how caps of different sizes can be applied to preform structure 102. Each of caps 104a-d provides a different amount of flexural reinforcement to heads 108, and therefore provides a respective fastener element 100 designed to provide a different amount of peel resistance. In this example, where each of caps 104a-d is formed from the same material, the largest cap 104a provides the greatest amount of reinforcement and the smallest cap 104d provides the least amount. Because the caps are freely formed structures, the size of the cap can be controlled by applying more or less liquid cap material to the head.

Figure 2A:
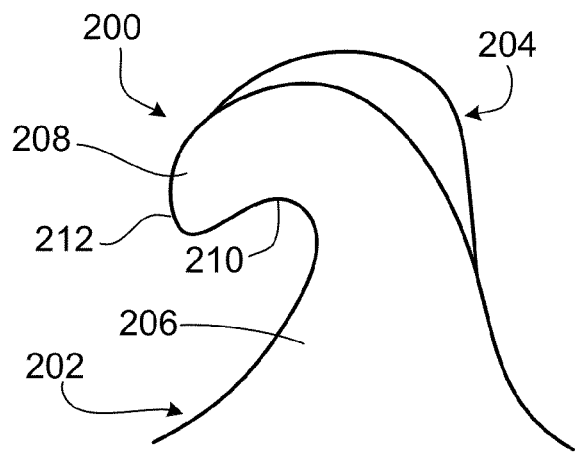
FIGS. 2A and 2B are side and end views, respectively, of a capped J-hook fastener element.
Figure 2B:
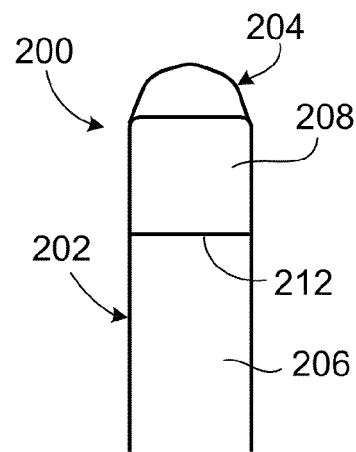

Referring next to FIGS. 2A and 2B, fastener element 200 includes a flexible preform structure 202 and a rigid cap 204 crowning the top of the preform structure. In this example, the preform structure has a J-shaped profile. Accordingly, preform structure 202 features a single head 208 that extends integrally from a tapered, upstanding stem 206. Head 208 extends laterally outward from stem 206 to overhang the supporting sheet-form base (not shown). Head 208 defines a crook 210 for engaging features of a mating fastener product and terminates in a distal re-entrant tip 212.

Cap 204 is situated atop preform structure 202 and bonded directly to the curved upper surface of head 208. As shown, the cap extends both upward and rearward from the upper surface of the head of the preform structure, but in this particular example does not extend beyond the flat sides of the preform structure and does not overhang the base sheet from which stem 206 extends. Cap 204 is positioned near the neck region of head 208, on the side opposite from crook 210, so as to brace the head against distension under peel loads. The cap is a free-form structure with a smooth convex outer surface. In another J-shaped example (not shown), the cap material does extend beyond the edges of the hook to overhang the base sheet.

Figure 3:
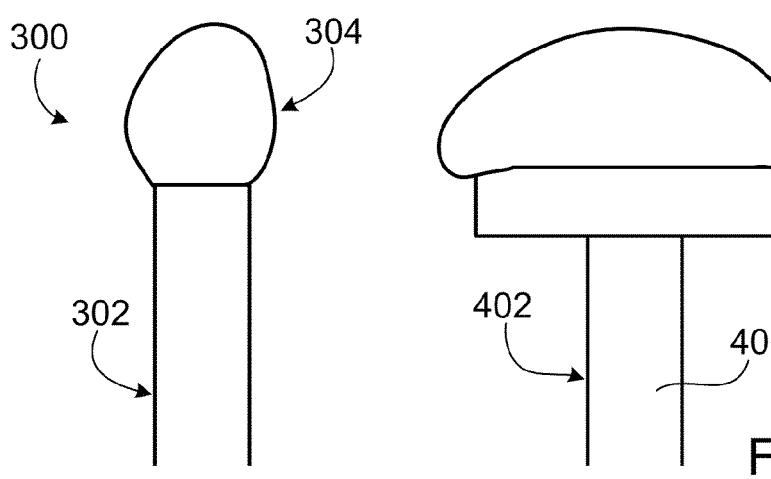
FIG. 3 is a side view of a capped stem fastener element.

Referring next to FIG. 3, fastener element 300 includes a flexible preform structure 302 and a rigid cap 304 crowning the top of the preform structure. In this example, the preform structure is a molded upstanding stem having a substantially constant rectangular or circular cross-section. This type of structure can be formed using a mold roll with stem shaped mold cavities. Cap 304 is situated atop preform structure 302 and bonded directly to the upper surface of the stem. The cap is a free-form structure with a smooth convex outer surface, forming a bulbous crown on the stem. As shown, the cap extends both upward and laterally outward beyond the upper surface of the head of the preform structure, to overhang the supporting base. The overhanging regions of cap 304 provide fastening features which may snag loop fibers, at least to resist shear loads.

Figure 4:
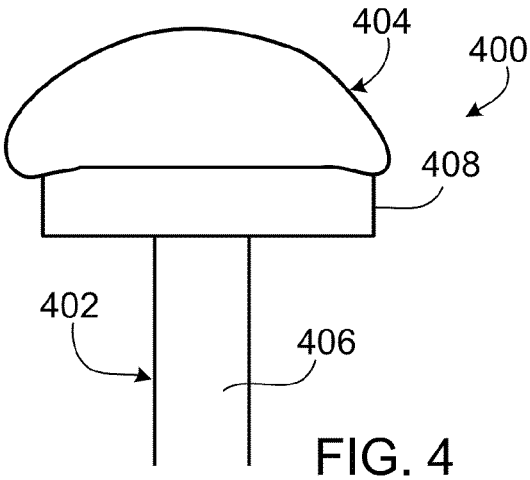
FIG. 4 is a side view of a capped mushroom fastener element.

Referring next to FIG. 4, fastener element 400 includes a flexible preform structure 402 and a rigid cap 404 crowning the top of the preform structure. In this example, the preform is a mushroom-type fastener component, featuring a straight, upstanding stem 406 supporting an enlarged head 408. Head 408 is a generally circular disk, such as may be formed by heating an upper part of the molded stem to soften the distal stem end, and then passing the softened stem end under a cold roll to cause the resin to flow radially outward. Head formation may alternatively be accomplished by passing the stem under a heated roll that applies both heat and pressure. Cap 404 is situated atop preform structure 402 and bonded directly to the flat upper surface of head 408. The cap is a free-form structure with a smooth convex outer surface, forming a bulbous crown on the stem. Further, as shown, the cap extends both upward and laterally outward beyond the upper surface of the head of the preform structure, to overhang the supporting base at least on one side, if not all the way around the head.

Figure 5A:
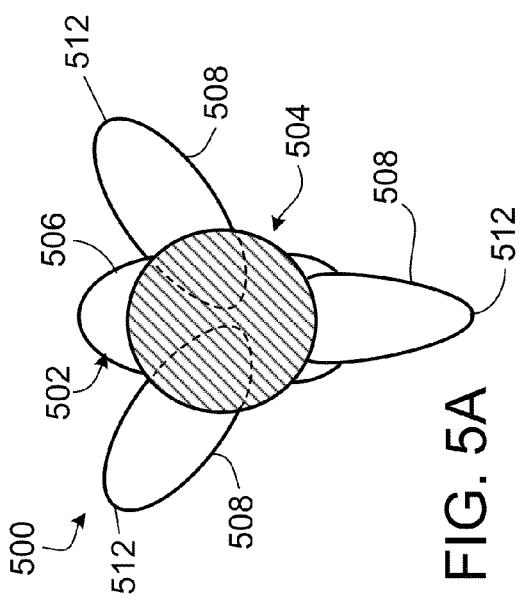
FIGS. 5A and 5B are top and side views, respectively, of a capped tri-lobal male fastener element.
Figure 5B:
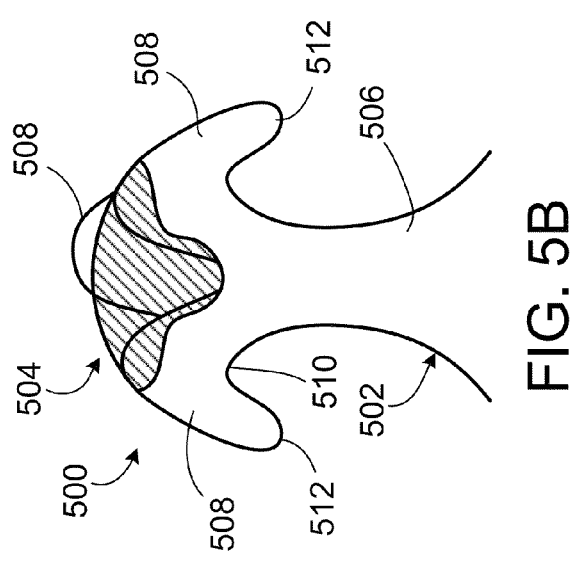

Referring to FIGS. 5A and 5B, fastener element 500 includes a flexible preform structure 502 and a rigid cap 504 crowning the top of the preform structure. In this example, the preform structure is a molded trident or a tri-lobal hook component. As such, preform structure 502 features three divergent heads 508 that extend integrally from a common upstanding stem 506 at 120 degree intervals. Heads 508 extend laterally outward from stem 506 to overhang the supporting sheet-form base in divergent lateral directions. Each of heads 508 defines a respective crook 510 for engaging features of a mating fastener product, and terminates in a distal re-entrant tip 512.

Cap 504 is situated atop preform structure 502 and bonded directly to the curved upper surfaces of heads 508. In particular, cap 504 is at least partially disposed in a recess defined between the divergent heads 508 of preform structure 502, so as to bridge a gap between the heads. The cap is a free-form structure with a smooth convex outer surface, forming a bulbous crown on top of the head of the preform structure. As shown, the cap extends upward to form the uppermost portion of fastener element 500, and portions of the cap bridging between adjacent heads overhang the base between the heads. As in the examples described above, cap 504 resists distension, or de-crooking, of each head under load from an engaged loop, thereby increasing the effective overall peel resistance of a field of such fastener elements.

Figure 6A:
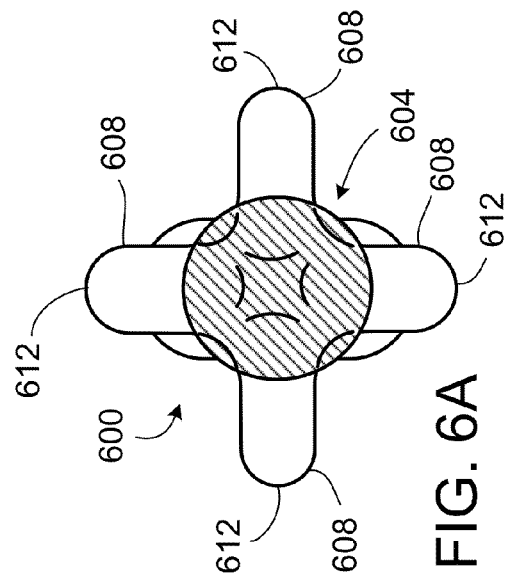
FIGS. 6A and 6B are top and side views, respectively, of a capped quadra-lobal male fastener element.
Figure 6B:
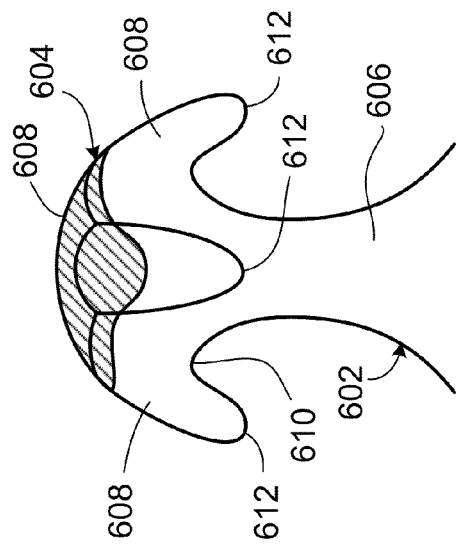

Referring to FIGS. 6A and 6B, fastener element 600 includes a flexible preform structure 602 and a rigid cap 604 crowning the top of the preform structure. In this example, the preform structure is a molded quad-lobal hook component. As such, preform structure 602 features four divergent heads 608 that extend integrally from a common upstanding stem 606 at 90 degree intervals. Heads 608 extend laterally outward from stem 606 to overhang the supporting sheet-form base in orthogonal lateral directions. Each of heads 608 defines a respective crook 610 for engaging features of a mating fastener product, and terminates in a distal re-entrant tip 612.

Cap 604 is situated atop preform structure 602 and bonded directly to the curved upper surfaces of heads 608. In particular, cap 604 is at least partially disposed in a recess defined between divergent heads 608 of preform structure 602, so as to bridge a gap between oppositely directed heads and also bridging between adjacent heads so as to form an additional overhang surface. The cap is a free-form structure with a smooth convex outer surface, forming a bulbous crown on top of the head of the preform structure. As shown, the cap extends both upward and laterally outward beyond the upper surfaces of the heads of the preform structure to overhang the lower portion of the stem and the base.

Each of touch fastener elements 500 and 600 feature preform structures with tapered heads that extend in multiple lateral directions. These types of preform structures can be molded using a mold roll including a multiplicity of precisely aligned mold plates, where each mold plate defines a cavity shaped to form a respective portion of the cross-machine direction features, such as is taught in U.S. Pat. No. 6,163,939, the entire teachings of which are incorporated herein by reference.

FIGS. 7A-7C, for example, show male touch fastener elements 700a-c in which the caps 704a-c essentially cover the heads 708a-c of the preform structures 702a-c. In this case, the rigid cap material at least partially covers the re-entrant tips of the heads, leaving the supporting stems free of cap material and flexible in response to bending loads.

The capping process may be controlled to limit the amount of material deposited on the preform structure, and the extent to which the material flows down the surfaces of the heads to envelop particular features. The latter may be advantageously altered by choice of material affinities and wetting properties, as discussed above, and also by structure surface finish and geometry.

Figure 8A:
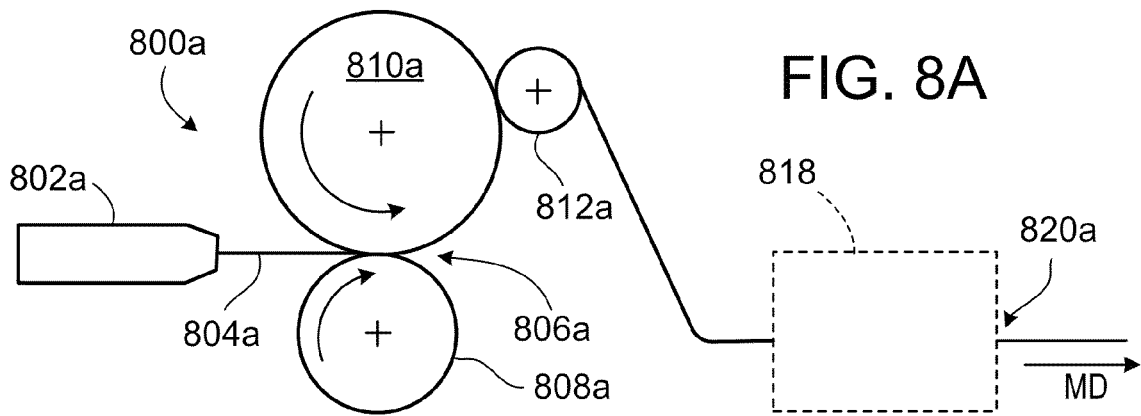
FIGS. 8A, 8B, and 8C are schematic views of systems for forming preform structures using a mold roll.

Many of the preform structures described above can be molded into the illustrated shapes. FIG. 8A illustrates a first example apparatus 800a and method for molding fastener element preforms together with a sheet-form base as a contiguous mass of resin. As shown, apparatus 800a includes an extruder 802a which provides a continuous sheet of molten thermoplastic resin 804a to a nip 806a formed between a pressure roll 808a and a counter-rotating mold roll 810a. The surface of the mold roll defines miniature blind-ended cavities that can be appropriately shaped to form the preform structures. Pressure in the nip causes thermoplastic resin 804a to enter the cavities of mold roll 810a to form the preform structures, while excess resin remains about the periphery of the mold roll and is molded between the rolls to form the supporting sheet-form base. The thermoplastic resin is cooled as it proceeds along the periphery of the mold roll, solidifying the preform structures, until it is stripped by stripper roll 812a. The product is a continuous preform strip 820a featuring an array of preform structures integrally formed on a flexible sheet-form base of resin. When forming hook-shaped preform structures (e.g., palm tree-shaped, J-shaped preforms, tri-lobal, or quad-lobal), the molded heads may distend during de-molding, but tend to recover substantially their as-molded shape. Further details regarding preform molding are described by U.S. Pat. Nos. 4,775,310, 6,802,260 and 6,163,939, the entire disclosures of which are hereby incorporated by reference.

In some embodiments, mold roll 810a comprises a face-to-face assembly of thin, circular plates or rings (not shown) that are, for example, about 0.003 inch to about 0.250 inch (0.0762 mm-6.35 mm) thick, some having cutouts in their periphery defining mold cavities and others having solid circumferences, serving to close the open sides of the mold cavities and serve as spacers, defining the spacing between adjacent rows in an array of preform structures. A fully "built up" mold roll may include ring stacks that have a width, for example, from about 0.75 inch to about 6 inches (1.91 cm-15.24 cm) or more and may contain, for example, from about 50 to 1000 or more individual rings. Further details regarding mold tooling are described by Fisher, U.S. Pat. No. 4,775,310. Additional tooling embodiments will also be described below.

Figure 8B:
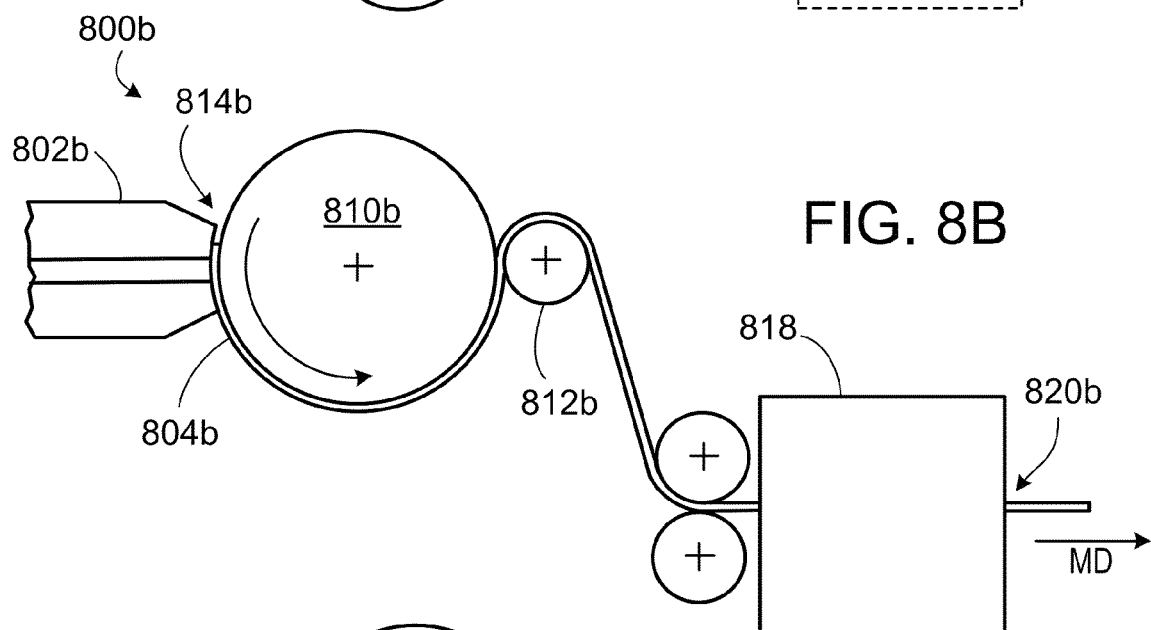

FIG. 8B illustrates a second example apparatus 800b designed for molding fastener element preforms together with a sheet-form base as a contiguous mass of resin. Apparatus 800b includes an extruder 802b designed to conform to the periphery of a mold roll 810b. As shown, a gap 814b is formed between extruder 802b and mold roll 810b. Extruder 802b provides a stream of molten thermoplastic resin 804b under pressure directly to gap 814b, forcing resin to enter the cavities of the mold roll. Excess resin remains about the periphery of the mold roll and is molded in the gap to form the supporting sheet-form base. As described above, the thermoplastic resin is cooled as it proceeds along the periphery of the mold roll, solidifying the preform structures, until it is stripped by stripper roll 812b. The product is a continuous preform strip 820b featuring an array of preform structures integrally formed on a flexible sheet-form base of resin. Further details regarding this process are described by Akeno, U.S. Pat. Nos. 5,781,969 and 5,913,482, the disclosures of which are hereby incorporated in full by reference.

Figure 8C:
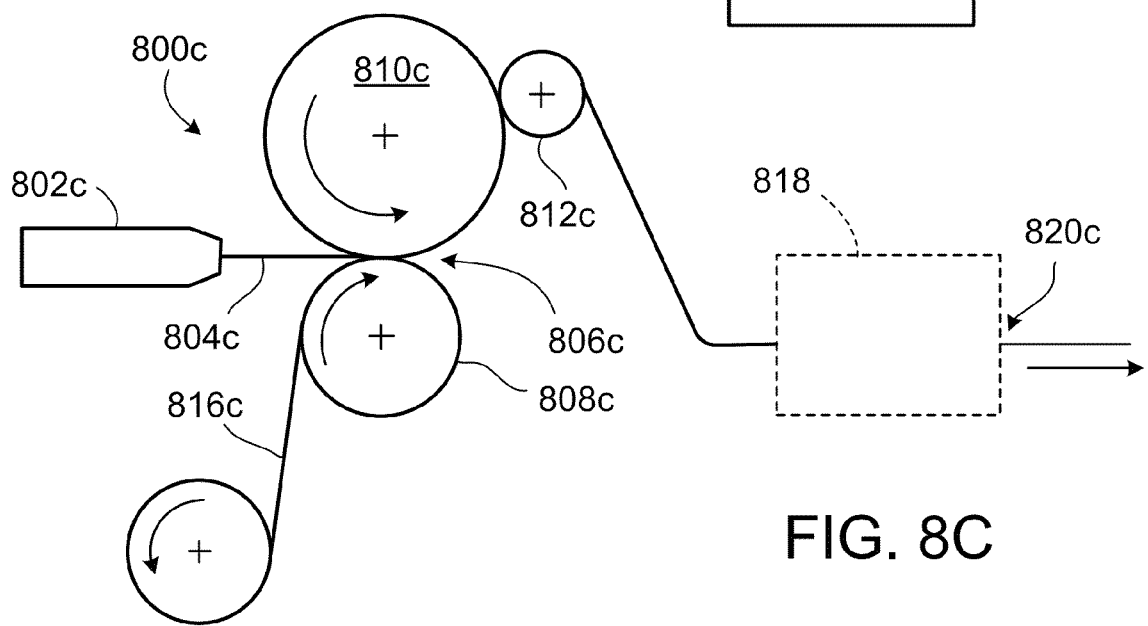

FIG. 8C illustrates a third example apparatus 800c designed for molding fastener element preforms while simultaneously bonding the preforms to a flexible substrate. Similar to the first example, apparatus 800c includes an extruder 802c in which provides a continuous sheet of molten thermoplastic resin 804c to a nip 806c formed between a pressure roll 808c and a counter-rotating mold roll 810c. In this example, the substrate material 816c is provided to nip 806c simultaneously with thermoplastic resin 804c. The heat and pressure in nip 806c causes substrate material 816c to become laminated and bonded to thermoplastic resin 804c as the preform structures are molded. The result can be a contiguous molded structure, without weld lines, extending from the tips of the preform structures into the substrate material, where the resin can intimately bond with, or encapsulate, features or fibers of the material to form a strong, permanent bond. The product is a continuous preform strip 820c featuring an array of preform structures integrally formed on a flexible substrate. Further details regarding this process are described by Kennedy et al., U.S. Pat. No. 5,260,015, the disclosure of which is hereby incorporated in full by reference. Other appropriate techniques are described in U.S. Pat. Nos. 7,048,818, 6,205,623, and 8,079,995, the disclosures of which are also hereby incorporate in full by reference.

FIG. 8D illustrates a fourth example apparatus 800d designed for forming fastener element preforms using a cut-and-stretch technique. Apparatus 800d includes an extruder 850 which forces thermoplastic resin through a die 852 having an opening shaped to form an elongated strip 854 featuring a thin base supporting multiple ribs in the shape of fastener elements. The ribs run parallel down the longitudinal direction of the strip. Strip 854 is pulled through a quench tank 856 by rollers 858. After quenching, strip 854 is fed to a cutter 860 designed to transversely slit or cut through the ribs at regular longitudinal intervals along the length of the ribs. The supporting base remains unmarked by the cutter. After the ribs have been cut, strip 854 is longitudinally stretched by nip rollers 862a and 862b, which are arranged in pairs of rollers driven at different surface speeds. Similar to the previous examples, the product is a continuous preform strip 820d featuring an array of preform structures integrally formed on a flexible substrate. Further details regarding this process are described by Nestegard, U.S. Pat. No. 4,894,060, the disclosure of which is hereby incorporated in full by reference.

In some cases, the preform structures are not molded in their final form. Accordingly, any of the apparatus disclosed above can include a processing station 818 to finalize the form of the preform structures. Such subsequent processing may include "flat-topping" hook-type preform structures, as described by Provost in U.S. Pat. No. 5,953,797, and by Akeno in U.S. Pat. No. 5,781,969, the entire disclosures of each of which are hereby incorporated by reference. In some cases, even straight molded stems may be subsequently processed to result in suitable fastener elements. In each of the processes discussed above, the preform product can proceed immediately from the preform processing apparatus to a station in which the caps are formed on the preform structures, thus producing the finished product in a single continuous process.

Of course, other suitable techniques and apparatus can be used for molding continuous strips carrying preform structures.

Figure 9B:
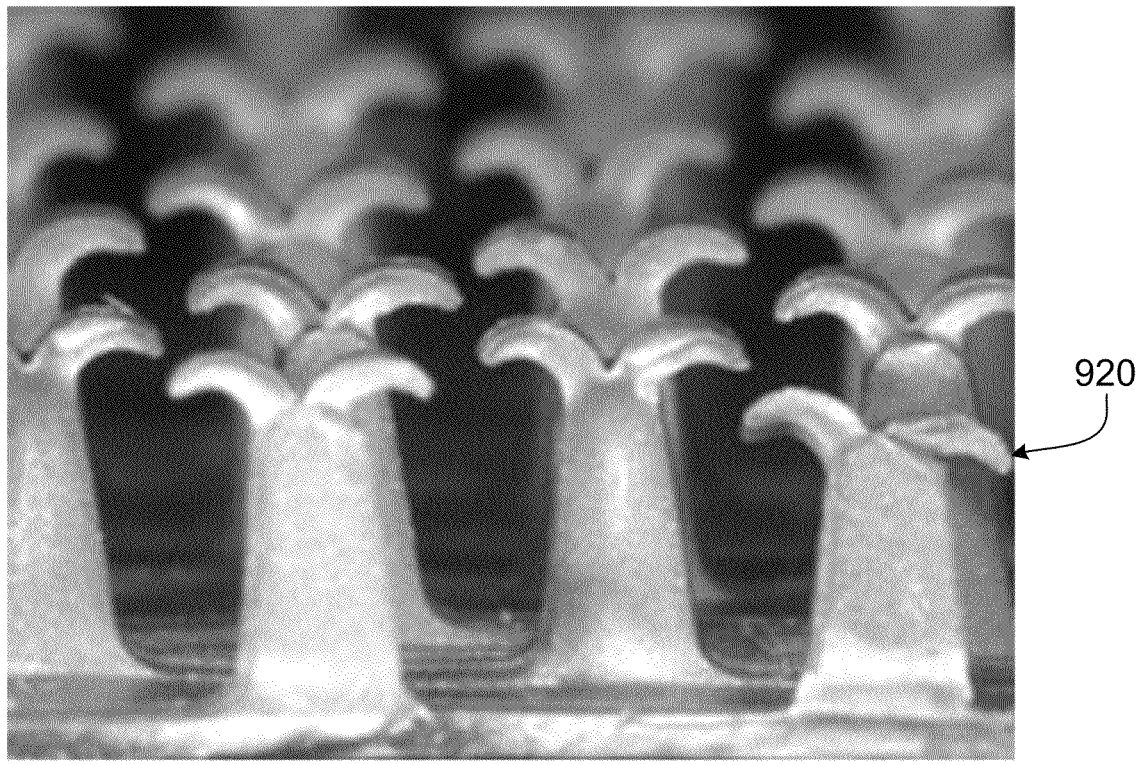
FIG. 9B is a photograph providing an enlarged perspective view of a product corresponding to the area marked FIG. 9B in FIG. 9A.

Referring to FIG. 9A, a continuous preform strip 920, such as may be formed using any of the above described apparatus and techniques, is carried in a feed direction along a guide roll 924. Guide roll 924 is arranged to convey preform strip 920 towards a rotating applicator drum 922. The preform strip is mounted such that its flexible base rides against the outer surface of the guide roll, while the preform structures extend outward to face the applicator drum. The applicator drum is designed to provide an open source of cap material for transfer onto at least some of the preform structures on the strip. As described in detail below, an exposed portion of the applicator drum surface carries a thin film of cap material to be deposited on the heads of the preform structures. Apparatus 900 is designed such that, as preform strip 920 passes across applicator drum 922, at least some of the cap material is drawn from the outer surface of the drum and onto the preform structures (see FIG. 9C).

As shown, applicator drum 922 is partially submerged in a bath of liquid cap material 926 contained in a relatively large trough 929. As the applicator drum rotates through the bath, liquid cap material is carried out of the trough on the outer surface of the drum. In some embodiments, the outer surface of the drum is modified to enhance the ability of the applicator drum to "pick up" the cap material. For example, the outer surface of the applicator drum can be scored or lightly engraved to provide a surface roughness. A doctor blade 929 can be used to remove excess cap material from the periphery of applicator drum 922, leaving a uniform, thin, liquid coating of cap material to coat the exposed drum outer surface. The positioning of the doctor blade with respect to the applicator drum is used to control the coating thickness.

Figure 16:
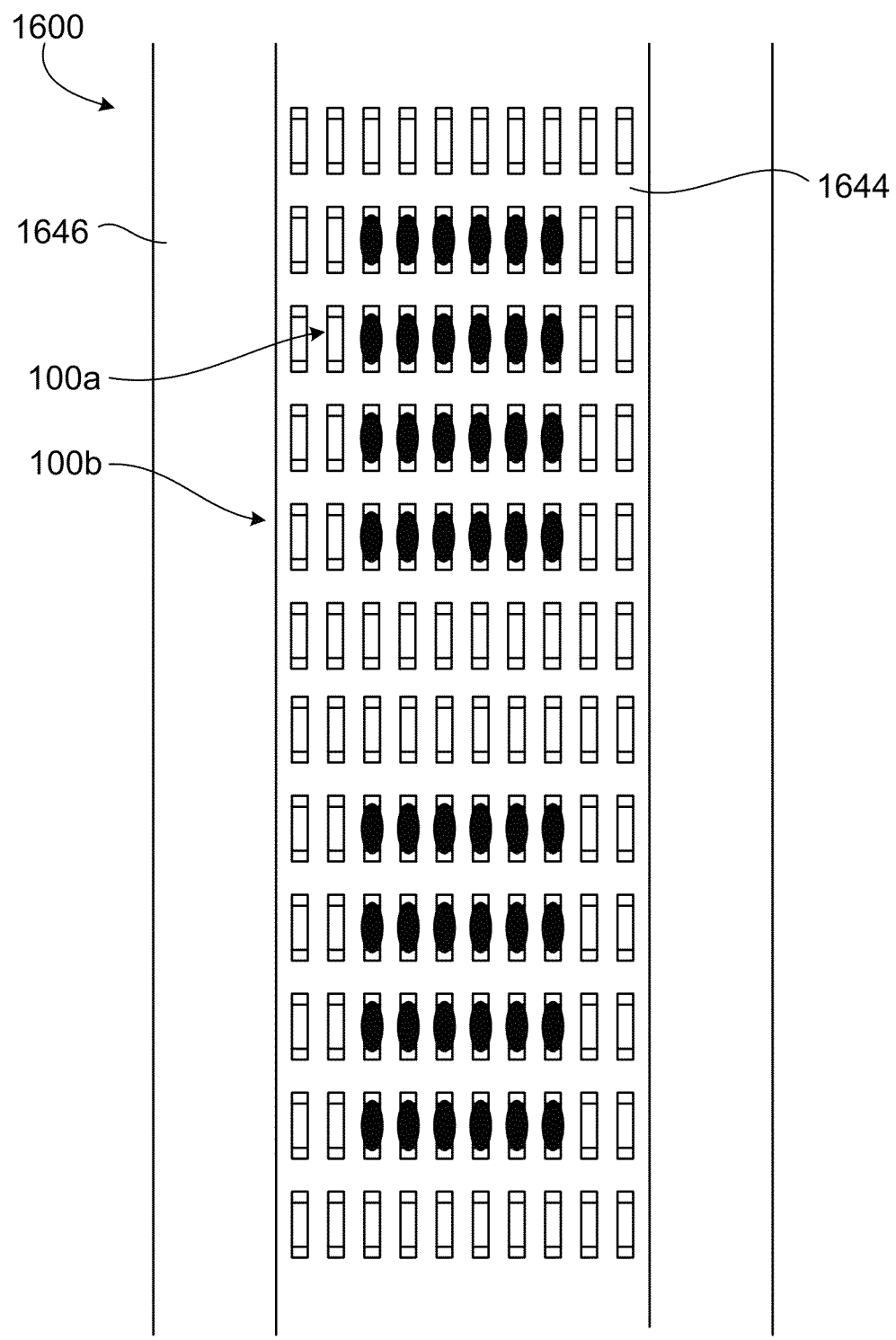
FIG. 16 is a top view of a fastener product featuring discrete regions of capped fastener elements surrounded by uncapped fastener elements.

Coating thickness is one of several process parameters that can affect the size and shape of the cap on the preform structures. For example, with all other variables being equal, a lower coating thickness would transfer less material to the preforms than a higher coating thickness. The coating thickness can vary across different embodiments based on, for example, the size and shape of the preform structures. In some implementations, the coating thickness is between about 0.005 and 0.01 inch. In one example, the coating thickness is about 0.003 inch. In another example, the coating thickness is about 0.04 inch. In this example, the entire periphery of roll 924 is coated. In other examples, the roll periphery features raised regions that pick up cap material for depositing on the preforms in desired areas (e.g., to form islands of capped stems, as shown in FIG. 16).

As noted above, the liquid cap material can be a molten thermoplastic resin. In some embodiments, a heater 930 (e.g., a resistive heater) is used to maintain the liquid cap material at a specified target temperature or within a target temperature range. The target temperature can, for example, be determined so as to maintain the cap material in liquid form. That is, the target temperature may be at least above the melting temperature of the cap material. As another example, the target temperature can be determined so as to maintain certain properties of the liquid cap material (e.g., viscosity, surface tension, etc.). In some embodiments, the applicator drum itself can be heated to maintain the temperature of the liquid cap material when it is carried from the trough on the outer surface of the drum.

Additives can be incorporated into the liquid cap material to improve its workability. For example, a thixotropic agent can be added to the liquid cap material to control its viscosity. In this case, the liquid cap material is thinner (i.e., having low viscosity) when agitated in the trough by the applicator drum, and thicker (i.e., having relative high viscosity) when resting on the surface of the applicator drum and deposited on the preform structures.

Figure 9D:
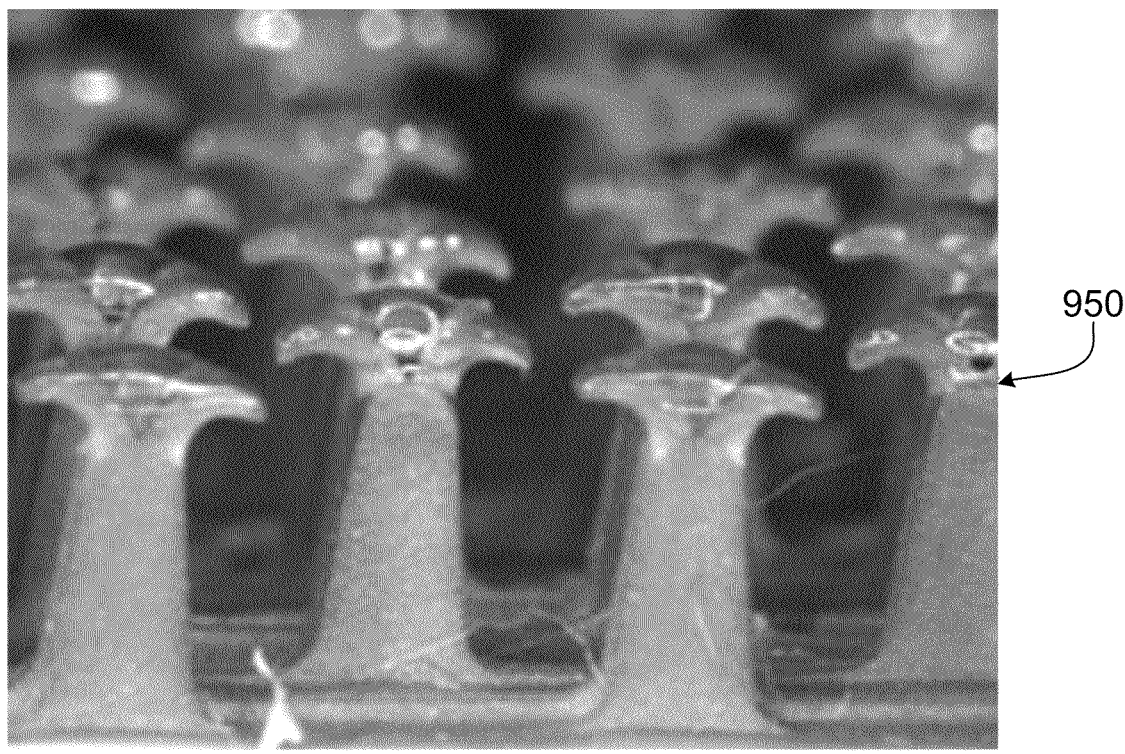
FIG. 9D is a photograph providing an enlarged perspective view of a product corresponding to the area marked FIG. 9D in FIG. 9A.

FIG. 9C shows the gap interface 832 between applicator drum 922 and guide roll 924. The gap is appropriately sized to receive the molded preform structures, bringing the structures into contact with the thin film of cap material as the preform strip passes adjacent to the outer surface of the applicator drum. In particular, as the heads of the preform structures briefly contact the film of cap material, a small amount of the substance is drawn off of the applicator drum and onto the preforms. Further, because there is little or no pressure exerted during the application process, the cap material is allowed to freely form on the outer surface of the preform structures to form the touch fastener product 950 (see FIG. 9D).

Referring back to FIG. 9A, one or more pre- or post-processing techniques can be implemented to supplement the above described technique for capping preform structures. For example, a pre-processing station 934 can be provided upstream of the applicator drum-guide roll interface. Pre-processing station 934 may implement a surface preparation technique on the preform structures to enhance the adhesion with the cap material. For example, the pre-processing station may implement a corona discharge or abrasive blasting technique to modify the surface energy of the preform structures. In some examples, a post-process station 936 can be provided downstream of the applicator drum-guide roll interface. Post-processing station 936 can be provided to cure the applied cap material, for example, using controlled ultraviolet radiation.

Figure 10A:
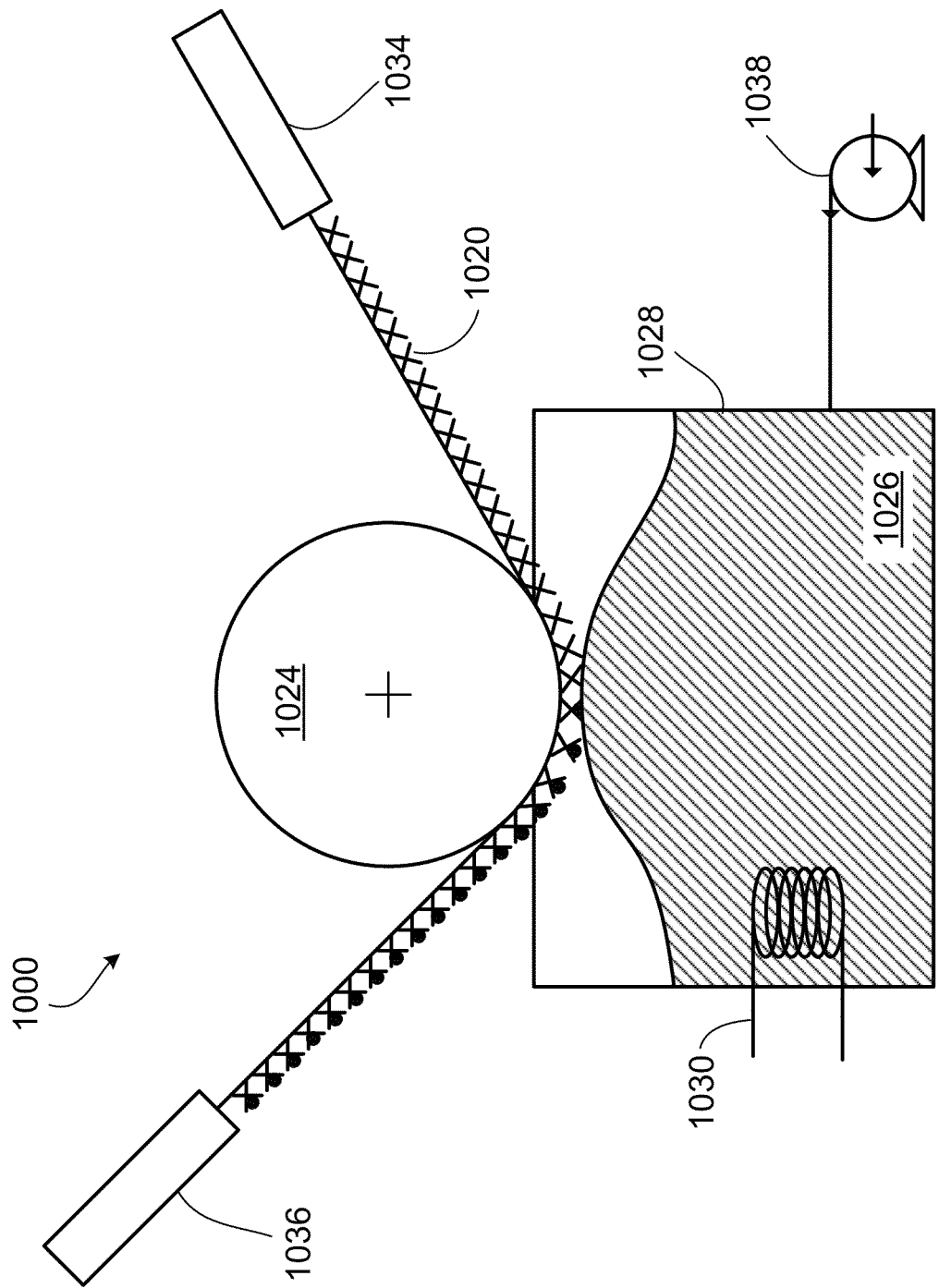
FIGS. 10A and 10B are schematic views of a second apparatus for capping preform structures.
Figure 10B:
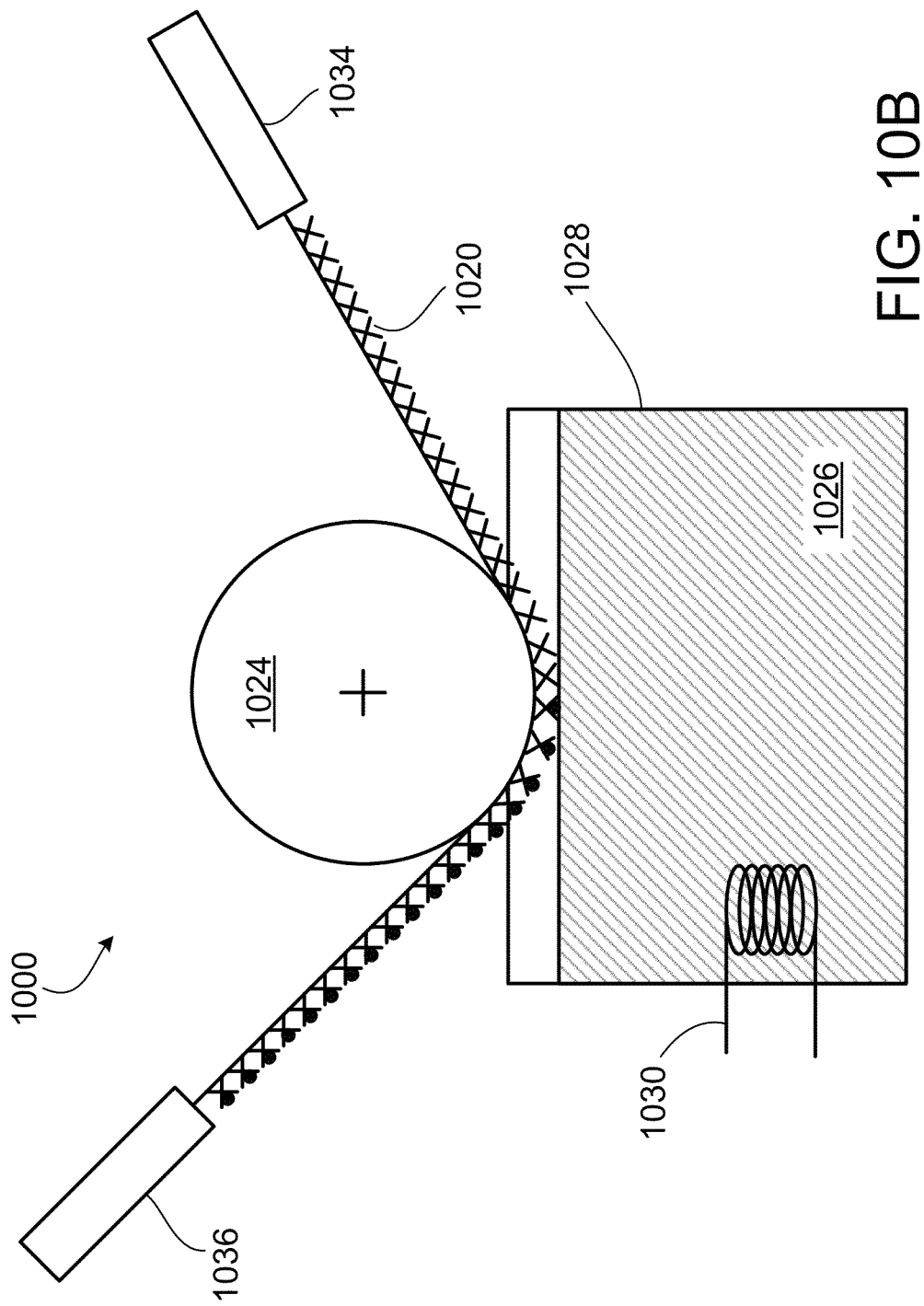

FIGS. 10A and 10B show an apparatus 1000 for implementing a dip or wave soldering technique for capping preform structures. As shown, a continuous preform strip 1020 is carried in a feed direction along the guide roll 1024. Guide roll 1024 is arranged to convey preform strip 1020 towards a bath of liquid cap material 1026 contained in a large trough 1028. The trough can include a heater 1030 for controlling the temperatures of the liquid cap material 1026. Similar to the previous example, the preform strip is mounted such that its flexible base rides against the outer surface of the guide roll, while the preform structures extend outward to face the trough and liquid bath. Apparatus 1000 is appropriately designed to allow guide roll 1024 to introduce outwardly extending structures of preform strip 1020 to enter trough 1028 and become at least partially submerged in the bath of liquid cap material 1026. As noted above, appropriate pre- and post-processing stations 1034 and 1036 can be provided to supplement this technique.

FIG. 10A shows an example where a wave pump 1038 is connected to trough 1028. The wave pump is designed to induce a substantially consistent wave of liquid cap material extend upward from the at rest surface of the bath. The pump can be controlled to maintain the height of the wave at an appropriate level. As shown, the structures of preform strip 1020 pass through the wave of liquid cap material 1026 and draw of a portion of the cap material on their overhanging heads. The cap material is allowed to freely form on the outer surface of the preform structures to form fasteners.

FIG. 10B shows an alternative example where the bath of liquid cap material 1026 is undisturbed in trough 1028. In this case, the heads of the preform structures on the continuous strip are simply dipped into the even level bath of cap material. The preform structures emerge from the dipping process with a portion of cap material deposited on the heads. The cap material is allowed to freely form on the outer surface of the preform structures to form fasteners.

FIGS. 11A and 11B show an apparatus 1100 for implementing a pin transfer technique for capping preform structures. As shown, a continuous preform strip 1120 is conveyed in a feed direction across an applicator plate 1140. The applicator plate includes a substantially planar substrate onto which a thin film or coating of liquid cap material 1126 is maintained. The preform strip is positioned such that the outwardly extending preform structures face downward, towards the face of the applicator plate. As shown, apparatus 1100 includes a plunger 1142 positioned above preform strip 1120 and aligned with applicator plate 1140. As the preform strip traverse the applicator plate, the plunger lightly presses down on the strip to force the preform structures on the strip into contact with the thin film of cap material (see FIG. 11B). When the pressure applied by the plunger is relieved, the preform strip is withdrawn from the applicator plate with the heads of the preform structures carrying a portion of the cap material on their outer surface. The cap material is allowed to freely form on the outer surface of the preform structures. As noted above, appropriate pre- and post-processing stations 1134 and 1136 can be provided to supplement this technique.

Of course other embodiments are also contemplated. For example, any of the above described techniques and apparatus can be modified to selectively apply the liquid cap material to the preform structures, such that at least some of the preforms are "capped", while others remain "uncapped".

FIG. 12A shows yet another example of a molded preform structure 1202 that can be used in conjunction with one or more implementations of the present disclosure. As shown, preform structure 1202 includes a broad stem 1206 and two outwardly extending heads 1208 contiguous with a distal end of the stem (similar to preform structure 102 shown in FIGS. 1A and 1B). In this example, the heads are relatively straight (without a re-entrant tip), extending both upward and laterally outward from the stem. This particular kind of preform structure may be particularly easy to remove from the cavities of a mold roll, due to the shape and directionality of the heads.

FIGS. 12B and 12C show a male touch fastener element 1200 that can be produced using the preform structure 1202. As one example, fastener element 1200 can be manufactured by depositing an amount of liquid cap material 1204 in the recess area 1214 between heads 1208, while simultaneously applying a downward force to deform the heads. This type of capping operation can be achieved, for example, using an appropriately configured applicator (e.g., an applicator drum or plunger, such as shown in FIGS. 9A, 11A, and 11B).

Figure 13A:
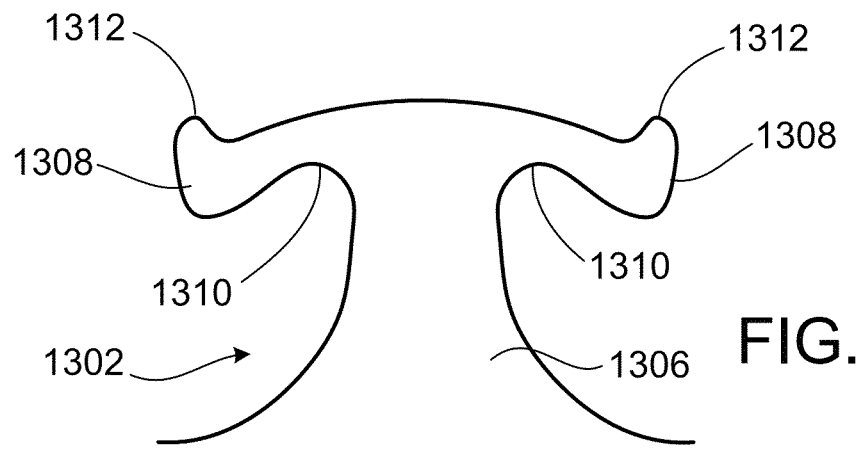
FIG. 13A is a side view of a preform structure formed using a cut-and-stretch technique.
Figure 13B:
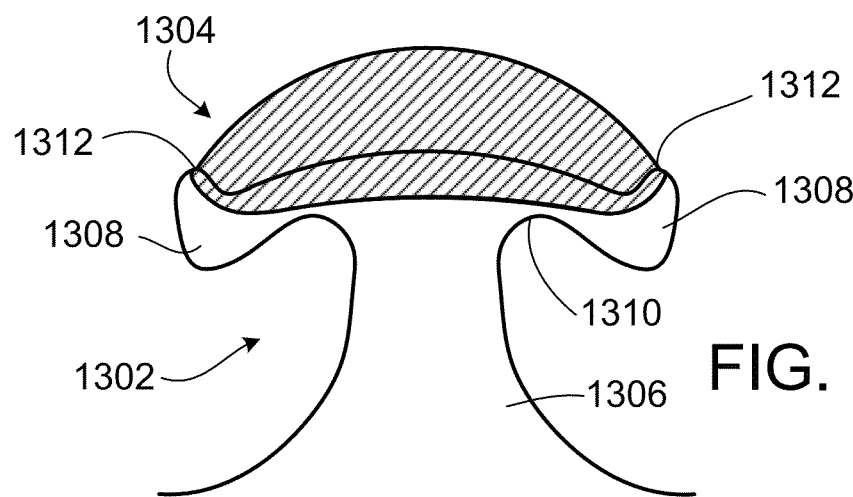
FIGS. 13B and 13C are side and front views, respectively, of capped fastener element including the preform structure of FIG. 13A.
Figure 13C:
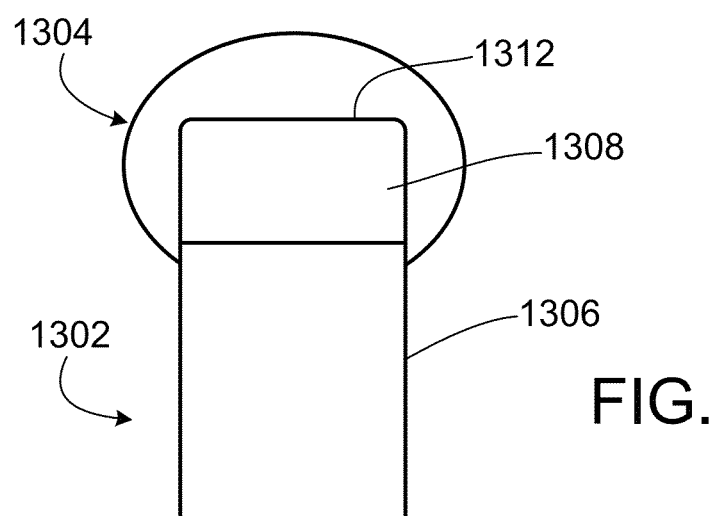

FIG. 13A shows an example of a preform structure 1302 formed using a cut-and-stretch technique, such as described above with respect to FIG. 8D. FIG. 13A may also be said to illustrate an extrusion die shape through which a continuous rail of resin is extruded. Similar to some previous examples, preform structure 1302 includes a stem 1306 and two outwardly extending heads 1308 contiguous with a distal end of the stem. Heads 1308 overhang the base of the strip (not shown) in the cross-machine direction, defining respective concave crooks 1310. In this example, due to the shape of the extrusion die, each of heads 1308 terminates in an upturned tip 1312 (as opposed to re-entrant tips, for example). As shown in FIG. 13B, the opposing upturned tips and the upper surface of the head provide a seat for the cap 1304. As shown most clearly in FIG. 13C, cap 1304 extends beyond the upper surface of heads 1308 to overhang the base in the machine direction to offer an additional engagement feature.

FIGS. 14A and 14B show a male touch fastener product 1400 designed to have a skin friendly feel to a user, while providing a strong engagement with a mating touch fastener (for example, inexpensive knit or non-woven materials). Such a fastener product can be manufactured using, for example, the techniques and apparatus described above. Accordingly, touch fastener 1400 includes a field of discrete male fastener elements 100 featuring soft, flexible hook-shaped preforms and smooth, rigid caps. The field of fastener elements extends broadly along the entire length and width of the sheet-form base. Fastener elements 100 extend outward from a sheet-form base 1444, and together with the base form a contiguous mass of resin.

FIGS. 15A and 15B show another male touch fastener product 1500, which is designed to be highly functional while providing a skin friendly feel. In this example, touch fastener product 1500 includes a flexible substrate 1546 and an array of fastener elements 100 arranged in a continuous lane along the length of the substrate. The width of the lane of fastener elements is less than that of the substrate, providing outer selvages that are free of any fastener elements. Fastener elements 100 extend from a solidified base layer 1544 of moldable resin that is intimately bonded to substrate 1546. Together, the fastener elements and the base layer are a contiguous mass of soft, flexible resin. As shown, the array includes an inner region of fastener elements 100a, each of which includes a rigid cap carried on an upper surface, and two outboard regions of fastener elements 100b that are uncapped. The outboard-uncapped regions are on either side of the inner-capped region.

This arrangement can provide a particular skin friendly feel, because the uncapped fastener elements on the edges of the array, which may seem significantly softer to a user, are more likely to contact the user's skin during use. In this case, the capped fastener elements provide the bulk of the fastening strength, while the uncapped fastener elements augment the skin friendly feel. This arrangement can also produce a fastener product that is particularly malleable, because the base layer from which the fastener elements extend is formed from a soft, flexible resin.

FIGS. 15C and 15D show yet another example male touch fastener product 1500'. In this example, the array fastener elements are arranged with caps oppositely to the example shown in FIGS. 15A and 15B. That is, in this case, the array of fastener elements includes an inner region of fastener elements 100a' that are uncapped, and two outboard regions of fastener elements 100b' that include the rigid caps on their upper surfaces. In this example, to provide a skin friendly feel, the cap material is softer than the material used to form the fastener element preforms.

FIG. 16 shows yet another male touch fastener product 1600, which is similar to touch fastener product 1200. For example, touch fastener product 1600 includes a flexible substrate 1646 and an array of fastener elements 100 arranged in a continuous lane lengthwise along the substrate. Fastener elements 100 extend integrally from a solidified base layer 1644. In this embodiment, there are several inner regions of capped fastener elements 100a, which form "islands" surrounded by a continuous outer region of uncapped fastener elements 100b. In another product (not illustrated), the preforms themselves are arranged only in separate regions, with all preforms capped. Such an arrangement allows the use, for example, of a cylindrical coating roll and provides regions between the capped stems that are void of preform elements.

Figure 17A:
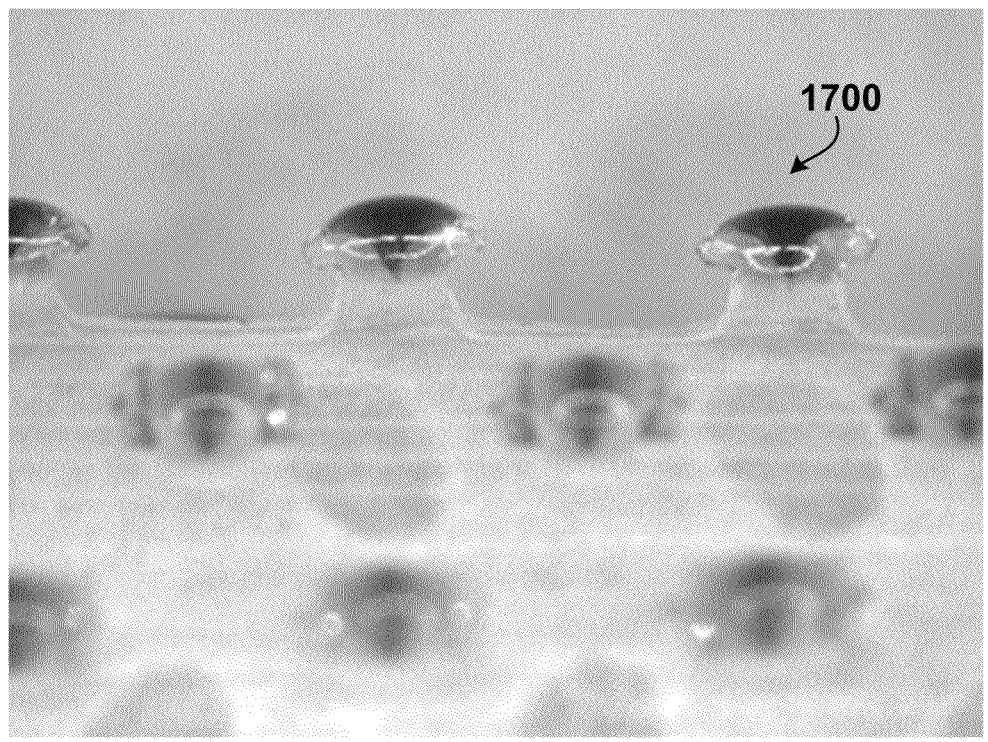
FIGS. 17A and 17B are photographs of a laminate touch fastener product with capped palm tree fastener elements.
Figure 17B:
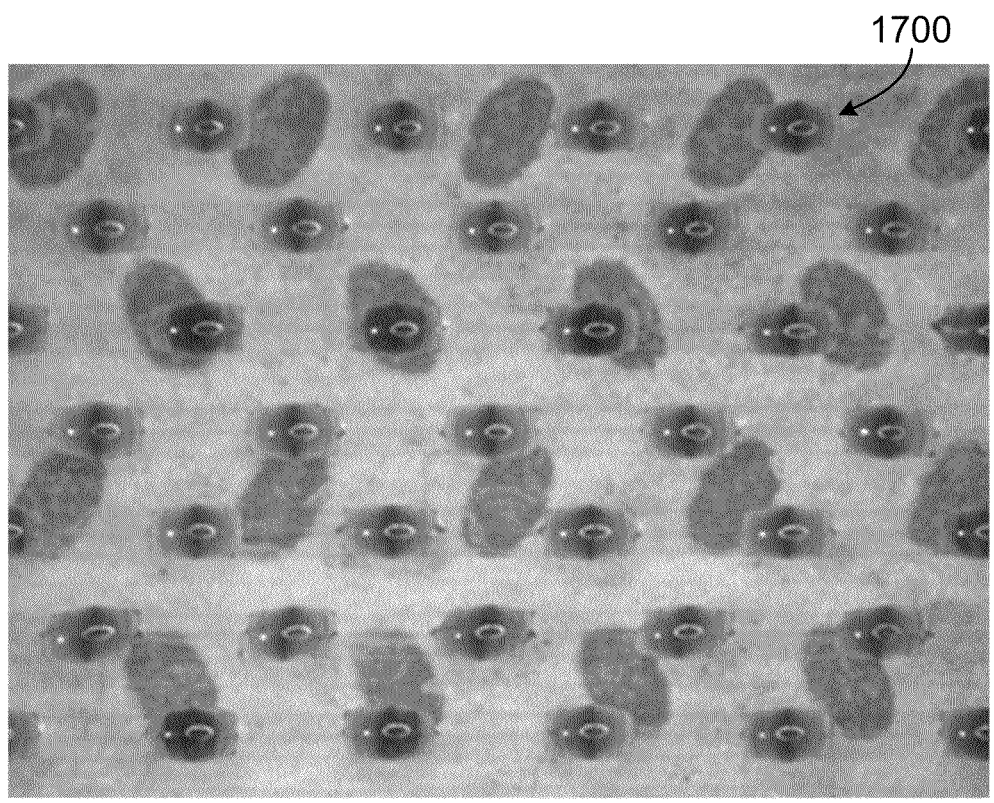

FIGS. 17A and 17B illustrate an example touch fastener product 1700 that can be manufactured using one or more of the described techniques. In particular, touch fastener product 1700 is similar to the diagram shown in FIGS. 15A-15D, and 16, where a field of fastener elements (in the form of capped preform structures) is supported on a flexible substrate. As in several other examples, the base layer of resin and the preform structures are molded from a soft flexible resin, while the caps are relatively rigid. This configuration allows the flexibility of the supporting substrate to be preserved, without sacrificing fastening performance. Also illustrated in this example is the use of a color additive in the cap material to provide a visual differentiation between the caps and the molded stems.

Figure 18A:
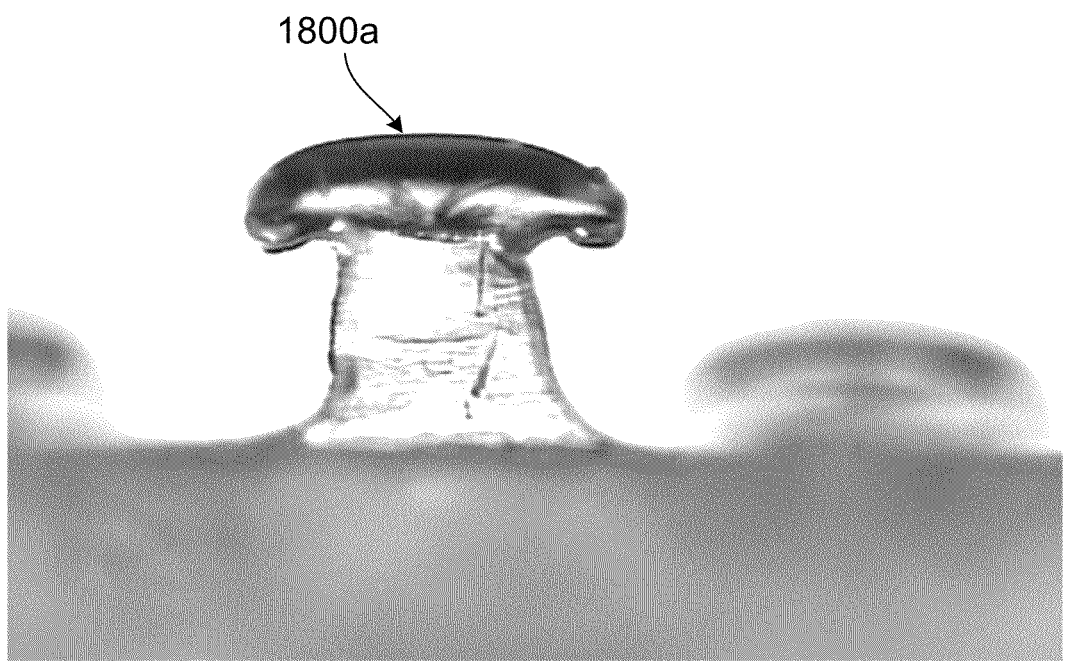
FIGS. 18A and 18B are photographs of side views of individual touch fastener elements featuring preformed structures with rigid caps.
Figure 18B:
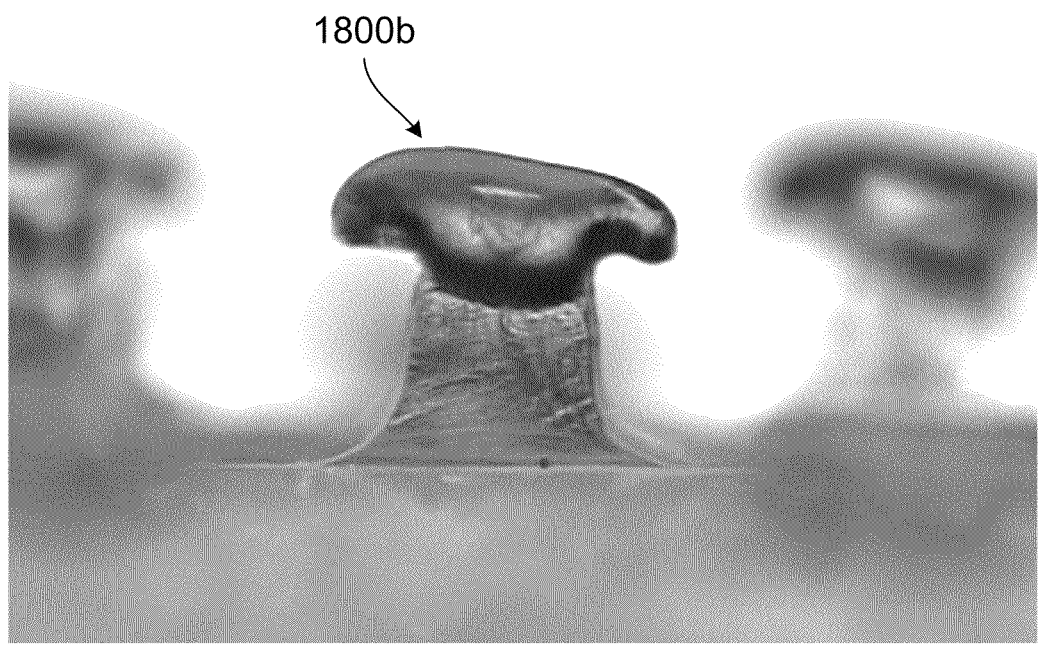

FIGS. 18A and 18B illustrate exemplary male touch fastener elements that can be manufactured using one or more of the above described techniques. In particular, FIG. 18A shows a fastener element 1800a that was formed in accordance with the diagram shown in FIGS. 1A and 1B, where the preform structure is a palm-tree shaped hook component and the rigid cap is situated in a recess between the divergent heads of the preform. As shown, at least a portion of the heads, the crooks, and the re-entrant tips of the preform structure are free of any cap material. FIG. 18B, on the other hand, shows a fastener element 1800b which is most similar to the diagram shown in FIG. 7A, where the rigid cap material at least partially covers the re-entrant tips of the heads of the palm-tree shaped preform structure. With all other variables being constant, fastener element 1800b will likely exhibit greater resistance to peel than fastener element 1800a, due to the increased rigidity provided by the larger cap. On the other hand, fastener element 1800a should provide a more skin friendly feel, because the tips of the heads, which are formed from an especially soft material, remain exposed for skin contact.

Figure 19:
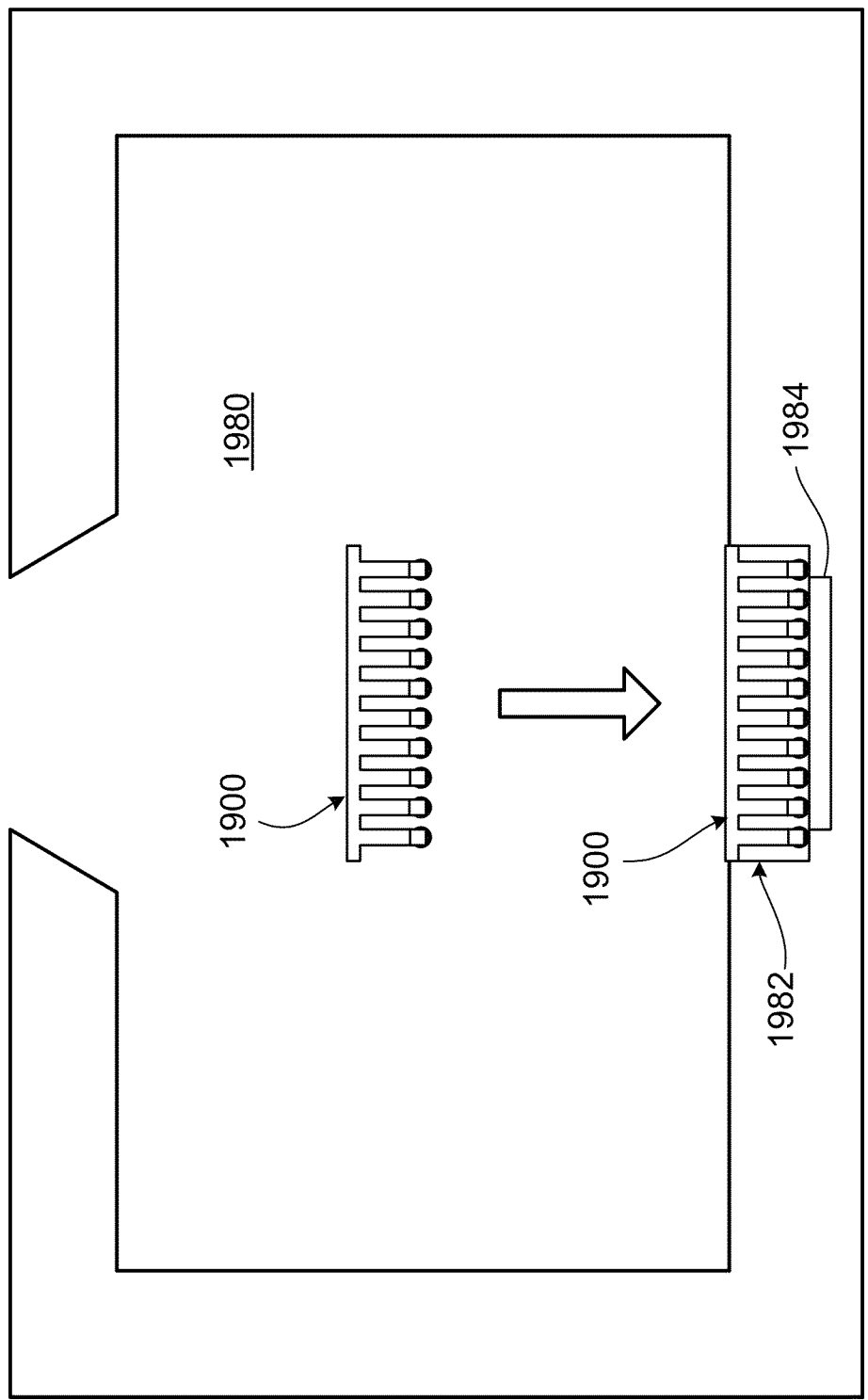
FIG. 19 is a schematic view of a touch fastener product with capped fastener elements being used in a foam molding application.

The touch fastening products described above may be used in a variety of fastening applications. FIG. 19 shows an example where a touch fastening product 1900 is adapted for use in a conventional foam molding or injection molding application. As shown, touch fastening product 1900 is inserted into a mold cavity 1980 and placed against the base of a trench 1982. The capped fastener elements of the product face the base of the trench. Touch fastener product 1900 is held against the base of trench 1982 by en embedded magnet 1984 that attracts the touch fastener product. In this example, the caps of the fastener elements contain a magnetically attractable substance (e.g., an iron powder) that causes the touch fastener product to be attracted to the magnet. In a particular example, the caps of the fastener elements are formed from a thermoplastic base resin such as EVA, in which iron particles have been suspended, such that the iron forms, for example, between 60 and 80 percent, by weight, of the cap material. This configuration is particularly cost effective (for example, compared to other techniques where the magnetically attractable material is incorporated with the base of the product) because the caps are closest to the magnet, thus optimizing attraction to the magnet at a relatively low material cost.

The use of terminology such as "front," "back," "top," "bottom," "over," "above," and "below" throughout the specification and claims is for describing the relative positions of various components of the system and other elements described herein. Similarly, the use of any horizontal or vertical terms to describe elements is for describing relative orientations of the various components of the system and other elements described herein. Unless otherwise stated explicitly, the use of such terminology does not imply a particular position or orientation of any component relative to the direction of the Earth gravitational force, or the Earth ground surface, or other particular position or orientation that the system and other elements may be placed in during operation, manufacturing, and transportation.

A number of embodiments of the invention have been described. Nevertheless, it will be understood that various modifications may be made without departing from the spirit and scope of the inventions.

What is claimed is:

1. A method of forming a touch fastener product having a sheet-form base and an array of discrete fastener elements each extending from the base, the method comprising:

providing a sheet-form base and an array of discrete fastener element preforms of resin, each preform extending from the base and comprising both a stem portion rising from the base and a head portion both contiguous with a distal end of the stem portion and having an upper surface directed away from the base, the head portion including at least one laterally directed extension overhanging the base in a primary lateral direction between exposed sides of the fastener element preform and ending at a distal, free tip; and then forming respective caps, of a cap material of a higher flex modulus than the resin of the preforms, on the upper surfaces of at least some of the fastener element preforms to form the discrete fastener elements, wherein the caps are formed to extend laterally beyond the exposed sides of the fastener element preforms.

2. The method of claim 1, wherein the caps are formed such that the tips of the head portions of the discrete fastener element preforms remain free of the cap material.

3. The method claim 1, wherein the caps are formed to extend laterally beyond the upper surfaces of the fastener element preforms, to overhang the base.

4. The method of claim 1, wherein the upper surface of each head portion, as provided, defines a central recess located between two extensions of the head portion and open on opposite sides of the fastener element preform, and wherein forming the caps comprises filling the central recesses, and wherein the caps are formed to have convex upper surfaces disposed over the recesses.

5. The method of claim 1, wherein the caps, as formed, extend farther from the base than the upper surfaces of the fastener element preforms.

6. The method of claim 1, wherein forming the caps comprises contacting the upper surfaces of the fastener element preforms with a quantity of liquid cap material carried on a cap material source, and then withdrawing the fastener element preforms from the cap material source, whereby a portion of the quantity of cap material is drawn off of the cap material source and remains on the fastener element preform.

7. The method of claim 6, wherein forming the caps further comprises allowing the cap material to form a free-form exposed cap surface on the fastener element preforms before solidifying.

8. The method of claim 6, wherein the cap material source comprises an outer surface of a rotating drum, and wherein forming the caps comprises passing the fastener element preforms adjacent the drum outer surface, such that cap material carried on the outer surfaces contacts the upper surfaces of the fastener element preforms.

9. The method of claim 1, wherein providing the molded sheet-form base and array of discrete fastener element preforms comprises continuously molding the sheet-form base and array of discrete fastener element preforms from a contiguous flow of resin.

10. A method of forming a touch fastener product having a sheet-form base and an array of discrete fastener elements each extending from the base, the method comprising:
    providing a sheet-form base and an array of discrete fastener element preforms of resin, each preform extending from the base and comprising both a stem portion rising from the base and a head portion both contiguous with a distal end of the stem portion and having an upper surface directed away from the base, the head portion including at least one laterally directed extension overhanging the base in a primary lateral direction between exposed sides of the fastener element preform and ending at a distal, free tip; and then
    forming respective caps, of a cap material of a higher flex modulus than the resin of the preforms, on the upper surfaces of at least some of the fastener element preforms to form the discrete fastener elements,
    wherein the caps are formed to extend laterally beyond the upper surfaces of the fastener element preforms, to overhang the base.

11. The method of claim 10, wherein the caps are formed such that the tips of the head portions of the discrete fastener element preforms remain free of the cap material.

12. The method of claim 10, wherein the upper surface of each head portion, as provided, defines a central recess located between two extensions of the head portion and open on opposite sides of the fastener element preform, and wherein forming the caps comprises filling the central recesses, and wherein the caps are formed to have convex upper surfaces disposed over the recesses.

13. The method of claim 10, wherein the caps, as formed, extend farther from the base than the upper surfaces of the fastener element preforms.

14. The method of claim 10, wherein forming the caps comprises contacting the upper surfaces of the fastener element preforms with a quantity of liquid cap material carried on a cap material source, and then withdrawing the fastener element preforms from the cap material source, whereby a portion of the quantity of cap material is drawn off of the cap material source and remains on the fastener element preform.

15. The method of claim 14, wherein forming the caps further comprises allowing the cap material to form a free-form exposed cap surface on the fastener element preforms before solidifying.

16. The method of claim 14, wherein the cap material source comprises an outer surface of a rotating drum, and wherein forming the caps comprises passing the fastener element preforms adjacent the drum outer surface, such that cap material carried on the outer surfaces contacts the upper surfaces of the fastener element preforms.

17. The method of claim 10, wherein providing the molded sheet-form base and array of discrete fastener element preforms comprises continuously molding the sheet-form base and array of discrete fastener element preforms from a contiguous flow of resin.

18. A method of forming a touch fastener product having a sheet-form base and an array of discrete fastener elements each extending from the base, the method comprising:
    providing a sheet-form base and an array of discrete fastener element preforms of resin, each preform extending from the base and comprising both a stem portion rising from the base and a head portion both contiguous with a distal end of the stem portion and having an upper surface directed away from the base, the head portion including two extensions separately overhanging the base in opposite lateral directions and ending at tips; and then
    forming respective caps, of a cap material of a higher flex modulus than the resin of the preforms, on the upper surfaces of at least some of the fastener element preforms to form the discrete fastener elements,
    wherein the upper surface of each head portion, as provided, defines a central recess located between the two extensions and open on opposite sides of the fastener element preform, and wherein forming the caps comprises filling the central recesses,
    wherein the caps are formed to extend laterally beyond exposed sides of the fastener element preforms, and
    wherein the caps are formed to extend laterally beyond the upper surfaces of the fastener element preforms, to overhang the base.

* * * * *